(12) United States Patent
Yamakawa et al.

(10) Patent No.: US 7,994,316 B2
(45) Date of Patent: Aug. 9, 2011

(54) 1,3,5-TRIAZINE DERIVATIVE, PRODUCTION METHOD THEREOF AND ORGANIC ELECTROLUMINESCENCE DEVICE COMPRISING THIS AS A COMPOSING COMPONENT

(75) Inventors: Tetsu Yamakawa, Tokyo (JP); Hidenori Aihara, Kanagawa (JP); Naoko Yanai, Tokyo (JP); Tsuyoshi Tanaka, Kanagawa (JP); Masaru Sato, Kanagawa (JP)

(73) Assignees: Tosoh Corporation, Yamaguchi (JP); Sagami Chemical Research Center, Kanagawa (JP)

( * ) Notice: Subject to any disclaimer, the term of this patent is extended or adjusted under 35 U.S.C. 154(b) by 611 days.

(21) Appl. No.: 12/064,867

(22) PCT Filed: Aug. 23, 2006

(86) PCT No.: PCT/JP2006/316469
§ 371 (c)(1),
(2), (4) Date: Feb. 26, 2008

(87) PCT Pub. No.: WO2007/023840
PCT Pub. Date: Mar. 1, 2007

(65) Prior Publication Data
US 2009/0281311 A1 Nov. 12, 2009

(30) Foreign Application Priority Data
Aug. 26, 2005 (JP) ................ 2005-246134
Apr. 24, 2006 (JP) ................ 2006-119912

(51) Int. Cl.
C07D 401/10 (2006.01)
C07D 401/14 (2006.01)
C07D 403/10 (2006.01)
C07D 403/14 (2006.01)
C09K 11/06 (2006.01)
H01L 51/50 (2006.01)

(52) U.S. Cl. ........................ 544/180; 313/504
(58) Field of Classification Search ............ 544/180
See application file for complete search history.

(56) References Cited

U.S. PATENT DOCUMENTS
6,225,467 B1    5/2001   Esteghamatian et al.

FOREIGN PATENT DOCUMENTS
JP  7-157473      6/1995
JP  2003-45662    2/2003
JP  2003-282270  10/2003
JP  2004-22334    1/2004

OTHER PUBLICATIONS
English language Abstract of JP2003-282270, Oct. 3, 2003.

English language Abstract of JP2004-22334, Jan. 22, 2004.
English language Abstract of JP 2003-45662, Feb. 14, 2003.
English language Abstract of JP 7-157473, Jun. 20, 1995.
V. Zamlynny et al., "PM FTIRRAS Studies of Potential-Controlled Transformations of a Monolayer and a Bilayer of 4-Pentadecylpyridine, a Model Surfactant, Adsorbed on a Au(111) Electrode Surface", Langmuir, 2003, 19, pp. 132-145.
T. Ishiyama et al., "Palladium(0)-Catalyzed Cross-Coupling Reaction of Alkoxydiboron with Haloarenes: A Direct Procedure for Arylboronic Esters", Journal of Organic Chemistry, 1995, 60, pp. 7508-7510.
Extended European Search Report for European Application No. 06782922.6 published May 13, 2011.
Gros et al., J. Org. Chem., 68, 2028-2029, 2003.

*Primary Examiner* — Venkataraman Balasubramanian
(74) *Attorney, Agent, or Firm* — Greenblum & Bernstein, P.L.C.

(57) ABSTRACT

Since the conventional electron transporters have low thermal stability, the organic electroluminescent devices using them are not sufficient in terms of the compatibility of their luminance and luminous efficiency with device lifetime.
A 1,3,5-triazine derivative of formula (1) is obtained by a metal catalyst-aided coupling reaction of a compound of formula (2) with a compound of formula (3), and this is used as a composing component of an organic electroluminescent device.

[Chem 1]

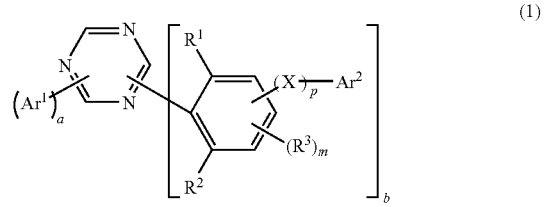

[Chem 2]

$$M \!-\! (X)_q \!-\! Ar^2 \quad (2)$$

[Chem 3]

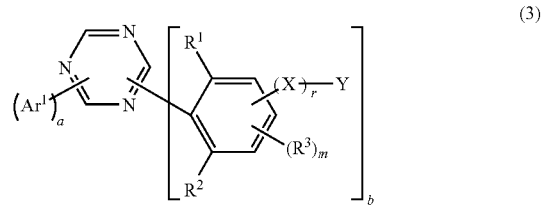

[In the formulae, $Ar^1$ and $Ar^2$ represent phenyl group or the like, $R^1$ and $R^2$ represent hydrogen atom or the like, $R^3$ represents methyl or the like, m is an integer of 0 to 2, X represents 2,4-pyridylene or the like, p is 1 or 2, a and b are 1 or 2, a+b is 3, q is 0 or an integer of p or less, M represents —$MgR^4$ group or the like, $R^4$ represents chlorine atom or the like, r is p-q, and Y represents a leaving group.]

20 Claims, 1 Drawing Sheet

1,3,5-TRIAZINE DERIVATIVE, PRODUCTION METHOD THEREOF AND ORGANIC ELECTROLUMINESCENCE DEVICE COMPRISING THIS AS A COMPOSING COMPONENT

TECHNICAL FIELD

This invention relates to a 1,3,5-triazine derivative, a production method thereof and an organic electroluminescence device which comprises this as a composing component.

BACKGROUND ART

Electroluminescence device has a structure in which an emissive layer containing a luminous compound is interposed between a hole transporting layer and an electron transporting layer. This is a device which uses, by further attaching an anode and a cathode to its sides, emission of light (fluorescence or phosphorescence) at the time of the deactivation of exciton formed when the positive hole and electron are injected into the fluorescent layer and recombined.

Though studies on the positive hole transporter for use in said device are in progress, studied cases of electron transporters are less and tris-(8-quinolinolato)aluminum (III) (Alq) has been used most generally, but a problem on its stability has been pointed out. On the other hand, a 1,3,5-triazine analogue is also one of the compounds expected as a long lifetime electron transporter because of the low energy level of the lowest unoccupied molecular orbital. For example, organic electroluminescent devices which comprise, as an electron transporter, a compound wherein a group in which an aromatic compound is connected to the 2-, 4- and 6-positions of the 1,3,5-triazine ring is substituted are disclosed in Patent References 1 to 4. However, examples are not clearly described regarding 1,3,5-triazine derivatives containing pyridyl group or pyridylene group. In addition, there are no clear descriptions in these Patent References regarding glass transition temperature, driving voltage and lifetime as indexes of device lifetime.

Patent Reference 1: U.S. Pat. No. 6,225,467
Patent Reference 2: JP-A-2003-045662
Patent Reference 3: JP-A-2003-282270
Patent Reference 4: JP-A-2004-022334

DISCLOSURE OF THE INVENTION

Problems that the Invention is to Solve

The conventional electron transporters have a problem of being low in thermal stability, and the organic electroluminescent devices using them are not sufficient in terms of the compatibility of their luminance and luminous efficiency with device lifetime.

Means for Solving the Problems

With the aim of solving the problems concerned in the stability of devices, the present inventors have conducted intensive studies by taking note of the effect of pyridyl group and found as a result that various synthesized 1,3,5-triazine derivatives containing pyridyl group or pyridylene group are thermally stable having both of the glass transition temperature and melting point of 100° C. or more. Also, thin film formation of these 1,3,5-triazine derivatives was possible by either a vacuum evaporation coating or spin coating method. In addition, it was found that when these are used as the electron transporter, a device which is excellent in terms of luminance, luminous efficiency, device lifetime and driving voltage in comparison with the organic electroluminescent device that uses the general electron transporter, Alq, can be prepared, thereby resulting in the accomplishment of the invention.

That is, the invention is a 1,3,5-triazine derivative which is represented by formula (1):

[Chem 1]

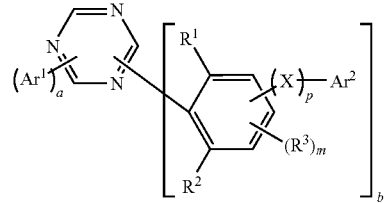

(1)

[in the formula, $Ar^1$ represents phenyl group, naphthylphenyl group, biphenylyl group or naphthyl group, which may be substituted with an alkyl group having from 1 to 6 carbon atom(s), $R^1$ and $R^2$ represent hydrogen atom or methyl group, $R^3$ represents an alkyl group having from 1 to 4 carbon atom(s), m is an integer of from 0 to 2, wherein $R^3$ may be the same or different from each other when m is 2; X represents 1,3-phenylene group, 1,4-phenylene group, 1,4-naphthylene group, 1,5-naphthylene group, 2,6-naphthylene group, 2,4-pyridylene group, 2,5-pyridylene group or 2,6-pyridylene group, which may be substituted with an alkyl group having from 1 to 4 carbon atom(s), p is 1 or 2 wherein X may be the same or different from each other when p is 2; $Ar^2$ represents phenyl group, 1-naphthyl group, 2-naphthyl group, 2-pyridyl group, 3-pyridyl group or 4-pyridyl group, which may be substituted with at least one alkyl group having from 1 to 6 carbon atom(s), with the proviso that at least one pyridine ring is contained in the substituent group $—(X)_p—Ar^2$, a and b are 1 or 2 wherein a+b is 3, $Ar^1$ may be the same or different from each other when a is 2, and $R^1$, $R^2$, $R^3$, m, X, p and $Ar^2$ may be the same or different from one another when b is 2].

Also, the invention is a production method, characterized in that the aforementioned 1,3,5-triazine derivative represented by the formula (1) is obtained by a coupling reaction, in the presence of a metal catalyst, of a substituted aromatic compound represented by formula (2):

[Chem 2]

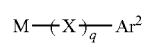

(2)

[in the formula, X and $Ar^2$ are as defined in the foregoing, q is 0 or an integer of p or less, M represents $—ZnR^4$ group, $—MgR^4$ group, $—SnR^5R^6R^7$ group, $—B(OH)_2$ group, $—B=R^8$ group, $—BF_3^-(Z^1)^+$ group or $—SiR^9R^{10}R^{11}$ group, $R^4$ represents chlorine atom, bromine atom or iodine atom, $R^5$, $R^6$ and $R^7$ represent an alkyl group having from 1 to 4 carbon atom(s), $R^8$ represents 2,3-dimethylbutane-2,3-dioxy group, ethylenedioxy group, 1,3-propanedioxy group or 1,2-phenylenedioxy group, $(Z^1)^+$ represents an alkali metal ion or a quaternary ammonium ion, and $R^9$, $R^{10}$ and $R^{11}$ represent methyl group, ethyl group, methoxy group, ethoxy group or chlorine atom] with a 1,3,5-triazine compound represented by formula (3):

[Chem 3]

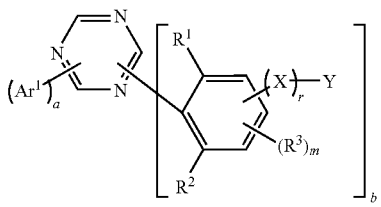

(3)

[in the formula, $Ar^1$, a, $R^1$, $R^2$, $R^3$, m, X and b are as defined in the foregoing, r is p-q, and Y represents a leaving group].

Further, the invention is a production method, characterized in that the aforementioned 1,3,5-triazine derivative represented by the formula (1) is obtained by a coupling reaction, in the presence of a metal catalyst, of a substituted 1,3,5-triazine compound represented by a formula (4):

[Chem 4]

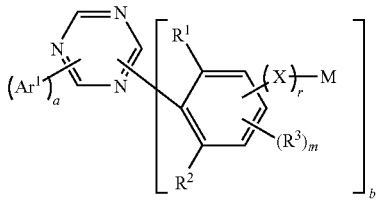

(4)

[in the formula, $Ar^1$, a, $R^1$, $R^2$, $R^3$, m, X, b, M and r are as defined in the foregoing] with an aromatic compound represented by formula (5):

[Chem 5]

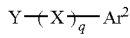

(5)

[in the formula, X, Y, q and $Ar^2$ are as defined in the foregoing].

In addition, the invention is an organic electroluminescence device which comprises the 1,3,5-triazine derivative represented by the formula (1) as a composing component.

Advantage of the Invention

The 1,3,5-triazine derivative of the invention represented by the formula (1) produces improvement of the electron injection efficiency and also lowering of the driving voltage when used as a composing component of an organic electroluminescence device. In addition, lowering of the driving voltage produces improvement of device lifetime. This is considered to be due to the ability of the nitrogen atom of pyridyl group possessed as a substituent group to undergo interaction with an electrode via its unshared electron pair (e.g., Langmuir, vol. 19, p. 132, 2003). Thus, an organic electroluminescence device having excellent luminescence characteristics and durability can be prepared by the use of the compound of the invention.

DESCRIPTION OF THE REFERENCE NUMERALS

Figure 1:
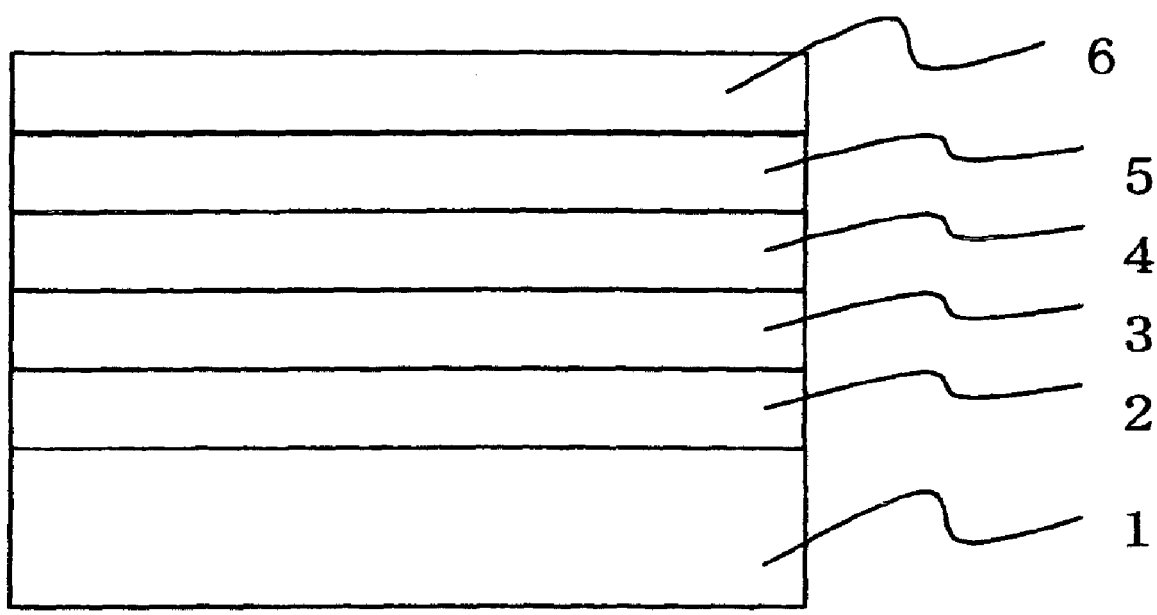
FIG. 1 is a sectional view of the organic electroluminescence device prepared in Example 23.

1. Glass substrate equipped with an ITO transparent electrode
2. Hole injection layer
3. Hole transporting layer
4. Emissive layer
5. Electron transporting layer
6. Cathode layer

BEST MODE FOR CARRYING OUT THE INVENTION

The following describes the invention further in detail.

As the phenyl group represented by $Ar^1$ which may be substituted with an alkyl group having from 1 to 6 carbon atom(s), phenyl group, p-tolyl group, m-tolyl group, o-tolyl group, 2,4-dimethylphenyl group, 3,5-dimethylphenyl group, mesityl group, 2-ethylphenyl group, 3-ethylphenyl group, 4-ethylphenyl group, 2,4-diethylphenyl group, 3,5-diethylphenyl group, 2-propylphenyl group, 3-propylphenyl group, 4-propylphenyl group, 2,4-dipropylphenyl group, 3,5-dipropylphenyl group, 2-isopropylphenyl group, 3-isopropylphenyl group, 4-isopropylphenyl group, 2,4-diisopropylphenyl group, 3,5-diisopropylphenyl group, 2-butylphenyl group, 3-butylphenyl group, 4-butylphenyl group and the like can be exemplified.

Also, 2,4-dibutylphenyl group, 3,5-dibutylphenyl group, 2-tert-butylphenyl group, 3-tert-butylphenyl group, 4-tert-butylphenyl group, 2,4-di-tert-butylphenyl group, 3,5-di-tert-butylphenyl group, 2-pentylphenyl group, 3-pentylphenyl group, 4-pentylphenyl group, 2,4-dipentylphenyl group, 3,5-dipentylphenyl group, 2-neopentylphenyl group, 3-neopentylphenyl group, 4-neopentylphenyl group, 2,4-dineopentylphenyl group, 3,5-dineopentylphenyl group, 2-hexylphenyl group, 3-hexylphenyl group, 4-hexylphenyl group, 2,4-dihexylphenyl group, 3,5-dihexylphenyl group, 2-cyclohexylphenyl group, 3-cyclohexylphenyl group, 4-cyclohexylphenyl group, 2,4-dicyclohexylphenyl group, 3,5-dicyclohexylphenyl group and the like can be exemplified.

From the viewpoint of good performance as the material for organic electroluminescence device, phenyl group, p-tolyl group, m-tolyl group, 4-ethylphenyl group, 4-propylphenyl group, 4-isopropylphenyl group, 4-butylphenyl group, 4-tert-butylphenyl group, 4-pentylphenyl group, 4-hexylphenyl group or 4-cyclohexylphenyl group is desirable, and phenyl group, p-tolyl group, m-tolyl group, 3,5-dimethylphenyl group, 4-butylphenyl group or 4-tert-butylphenyl group is further desirable.

As the naphthylphenyl group represented by $Ar^1$ which may be substituted with an alkyl group having from 1 to 6 carbon atom(s), 4-(1-naphthyl)phenyl group, 4-(2-naphthyl)phenyl group, 3-(1-naphthyl)phenyl group, 3-(2-naphthyl)phenyl group, 4-(4-methylnaphthalen-1-yl)phenyl group, 3-(4-methylnaphthalen-1-yl)phenyl group, 2-methyl-4-(1-naphthyl)phenyl group, 2-methyl-4-(2-naphthyl)phenyl group, 5-methyl-3-(1-naphthyl)phenyl group and 5-methyl-3-(2-naphthyl)phenyl group and the like can be exemplified. From the viewpoint of good performance as the material for organic electroluminescence device, 4-(1-naphthyl)phenyl group, 4-(2-naphthyl)phenyl group, 3-(1-naphthyl)phenyl group or 3-(2-naphthyl)phenyl group is desirable.

As the biphenylyl group represented by $Ar^1$ which may be substituted with an alkyl group having from 1 to 6 carbon atom(s), 4-biphenylyl group, 4'-methylbiphenyl-4-yl group, 4'-ethylbiphenyl-4-yl group, 4'-propylbiphenyl-4-yl group, 4'-butylbiphenyl-4-yl group, 4'-tert-butylbiphenyl-4-yl group, 4'-hexylbiphenyl-4-yl group, 3-biphenylyl group, 3'-methylbiphenyl-3-yl group, 3'-ethylbiphenyl-3-yl group, 3'-propylbiphenyl-3-yl group, 3'-butylbiphenyl-3-yl group, 3'-tert-butylbiphenyl-3-yl group, 3'-hexylbiphenyl-3-yl group and the like can be exemplified. From the viewpoint of good performance as the material for organic electroluminescence device, 4-biphenylyl group, 4'-methylbiphenyl-4-yl group, 4'-tert-butylbiphenyl-4-yl group, 3-biphenylyl group, 3'-methylbiphenyl-3-yl group or 3'-tert-butylbiphenyl-3-yl group is desirable, and 4-biphenylyl group or 3-biphenylyl group is further desirable.

As the naphthyl group represented by $Ar^1$ which may be substituted with an alkyl group having from 1 to 6 carbon atom(s), 1-naphthyl group, 4-methylnaphthalen-1-yl group, 4-ethylnaphthalen-1-yl group, 4-propylnaphthalen-1-yl group, 4-butylnaphthalen-1-yl group, 4-tert-butylnaphthalen-1-yl group, 4-hexylnaphthalen-1-yl group, 5-methylnaphthalen-1-yl group, 5-ethylnaphthalen-1-yl group, 5-propylnaphthalen-1-yl group, 5-butylnaphthalen-1-yl group, 5-tert-butylnaphthalen-1-yl group, 5-hexylnaphthalen-1-yl group, 2-naphthyl group, 6-methylnaphthalen-2-yl group, 6-ethylnaphthalen-2-yl group, 6-propylnaphthalen-2-yl group, 6-butylnaphthalen-2-yl group, 6-tert-butylnaphthalen-2-yl group, 6-hexylnaphthalen-2-yl group, 7-methylnaphthalen-2-yl group, 7-ethylnaphthalen-2-yl group, 7-propylnaphthalen-2-yl group, 7-butylnaphthalen-2-yl group, 7-tert-butylnaphthalen-2-yl group, 7-hexylnaphthalen-2-yl group and the like can be exemplified.

From the viewpoint of good performance as the material for organic electroluminescence device, 1-naphthyl group, 4-methylnaphthalen-1-yl group, 4-tert-butylnaphthalen-1-yl group, 5-methylnaphthalen-1-yl group, 5-tert-butylnaphthalen-1-yl group, 2-naphthyl group, 6-methylnaphthalen-2-yl group, 6-tert-butylnaphthalen-2-yl group, 7-methylnaphthalen-2-yl group or 7-tert-butylnaphthalen-2-yl group is desirable, and 1-naphthyl group or 2-naphthyl group is further desirable.

From the viewpoint of good performance as the material for organic electroluminescence device, hydrogen atom is desirable as the $R^1$ and $R^2$.

As the alkyl group having from 1 to 4 carbon atom(s) represented by $R^3$, methyl group, ethyl group, propyl group, isopropyl, cyclopropyl group, butyl group, isobutyl group, sec-butyl group, tert-butyl group, cyclobutyl group, cyclopropylmethyl group and the like can be exemplified.

From the viewpoint of good performance as the material for organic electroluminescence device, m is desirably 0 or 1, more desirably 0.

As X, 1,3-phenylene group, 2-methyl-1,13-phenylene group, 4-methyl-1,3-phenylene group, 5-methyl-1,3-phenylene group, 2-tert-butyl-1,3-phenylene group, 4-tert-butyl-1,3-phenylene group, 5-tert-butyl-1,3-phenylene group, 1,4-phenylene group, 2-methyl-1,4-phenylene group, 2-tert-butyl-1,4-phenylene group, 1,4-naphthylene group, 2-methyl-1,4-naphthylene group, 5-methyl-1,4-naphthylene group, 6-methyl-1,4-naphthylene group, 1,4-naphthylene group, 2-tert-butyl-1,4-naphthylene group, 5-tert-butyl-1,4-naphthylene group, 6-tert-butyl-1,4-naphthylene group, 1,5-naphthylene group, 2-methyl-1,5-naphthylene group, 3-methyl-1,5-naphthylene group, 4-methyl-1,5-naphthylene group, 2-tert-butyl-1,5-naphthylene group, 3-tert-butyl-1,5-naphthylene group, 4-tert-butyl-1,5-naphthylene group and the like can be exemplified.

Moreover, 2,6-naphthylene group, 1-methyl-2,6-naphthylene group, 3-methyl-2,6-naphthylene group, 4-methyl-2,6-naphthylene group, 1-tert-butyl-2,6-naphthylene group, 3-tert-butyl-2,6-naphthylene group, 4-tert-butyl-2,6-naphthylene group, 2,4-pyridylene group, 3-methyl-2,4-pyridylene group, 5-methyl-2,4-pyridylene group, 6-methyl-2,4-pyridylene group, 3-tert-butyl-2,4-pyridylene group, 5-tert-butyl-2,4-pyridylene group, 6-tert-butyl-2,4-pyridylene group, 2,5-pyridylene group, 3-methyl-2,5-pyridylene group, 4-methyl-2,5-pyridylene group, 6-methyl-2,5-pyridylene group, 3-tert-butyl-2,5-pyridylene group, 4-tert-butyl-2,5-pyridylene group, 6-tert-butyl-2,5-pyridylene group, 2,6-pyridylene group, 3-methyl-2,6-pyridylene group, 4-methyl-2,6-pyridylene group, 3-tert-butyl-2,6-pyridylene group, 4-tert-butyl-2,6-pyridylene group and the like can be exemplified.

From the viewpoint of good performance as the material for organic electroluminescence device, 1,4-phenylene group, 2,5-pyridylene group or 2,6-pyridylene group is desirable.

As $Ar^2$, phenyl group, p-tolyl group, m-tolyl group, o-tolyl group, 2,4-dimethylphenyl group, 3,5-dimethylphenyl group, mesityl group, 2-ethylphenyl group, 3-ethylphenyl group, 4-ethylphenyl group, 2,4-diethylphenyl group, 3,5-diethylphenyl group, 2-propylphenyl group, 3-propylphenyl group, 4-propylphenyl group, 2,4-dipropylphenyl group, 3,5-dipropylphenyl group, 2-isopropylphenyl group, 3-isopropylphenyl group, 4-isopropylphenyl group, 2,4-diisopropylphenyl group, 3,5-diisopropylphenyl group, 2-butylphenyl group, 3-butylphenyl group, 4-butylphenyl group, 2,4-dibutylphenyl group, 3,5-dibutylphenyl group, 2-tert-butylphenyl group, 3-tert-butylphenyl group, 4-tert-butylphenyl group and the like can be exemplified.

Moreover, 2,4-di-tert-butylphenyl group, 3,5-di-tert-butylphenyl group, 2-pentylphenyl group, 3-pentylphenyl group, 4-pentylphenyl group, 2,4-dipentylphenyl group, 3,5-dipentylphenyl group, 2-neopentylphenyl group, 3-neopentylphenyl group, 4-neopentylphenyl group, 2,4-dineopentylphenyl group, 3,5-dineopentylphenyl group, 2-hexylphenyl group, 3-hexylphenyl group, 4-hexylphenyl group, 2,4-dihexylphenyl group, 3,5-dihexylphenyl group, 2-cyclohexylphenyl group, 3-cyclohexylphenyl group, 4-cyclohexylphenyl group, 2,4-dicyclohexylphenyl group, 3,5-dicyclohexylphenyl group, 1-naphthyl group, 4-methylnaphthalen-1-yl group, 4-ethylnaphthalen-1-yl group, 4-propylnaphthalen-1-yl group, 4-butylnaphthalen-1-yl group and the like can be exemplified.

Moreover, 4-tert-butylnaphthalen-1-yl group, 4-hexylnaphthalen-1-yl group, 5-methylnaphthalen-1-yl group, 5-ethylnaphthalen-1-yl group, 5-propylnaphthalen-1-yl group, 5-butylnaphthalen-1-yl group, 5-tert-butylnaphthalen-1-yl group, 5-hexylnaphthalen-1-yl group, 2-naphthyl group, 6-methylnaphthalen-2-yl group, 6-ethylnaphthalen-2-yl group, 6-propylnaphthalen-2-yl group, 6-butylnaphthalen-2-yl group, 6-tert-butylnaphthalen-2-yl group, 6-hexylnaphthalen-2-yl group, 7-methylnaphthalen-2-yl group, 7-ethylnaphthalen-2-yl group, 7-propylnaphthalen-2-yl group, 7-butylnaphthalen-2-yl group, 7-tert-butylnaphthalen-2-yl group, 7-hexylnaphthalen-2-yl group and the like can be exemplified.

Moreover, 2-pyridyl group, 3-methylpyridin-2-yl group, 4-methylpyridin-2-yl group, 5-methylpyridin-2-yl group, 6-methylpyridin-2-yl group, 3-ethylpyridin-2-yl group, 4-ethylpyridin-2-yl group, 5-ethylpyridin-2-yl group, 6-ethylpyridin-2-yl group, 3-propylpyridin-2-yl group, 4-propylpyridin-2-yl group, 5-propylpyridin-2-yl group, 6-propylpyridin-2-yl group, 3-buthylpyridin-2-yl group, 4-buthylpyridin-2-yl group, 5-buthylpyridin-2-yl group, 6-buthylpyridin-2-yl group, 3-tert-butylpyridin-2-yl group, 4-tert-butylpyridin-2-yl group, 5-tert-butylpyridin-2-yl group, 6-tert-butylpyridin-2-yl group, 3-pyridyl group, 2-methylpyridin-3-yl group, 4-methylpyridin-3-yl group, 5-methylpyridin-3-yl group, 6-methylpyridin-3-yl group, 2-ethylpyridin-3-yl group and the like can be exemplified.

Moreover, 4-ethylpyridin-3-yl group, 5-ethylpyridin-3-yl group, 6-ethylpyridin-3-yl group, 2-propylpyridin-3-yl group, 4-propylpyridin-3-yl group, 5-propylpyridin-3-yl group, 6-propylpyridin-3-yl group, 2-butylpyridin-3-yl group, 4-butylpyridin-3-yl group, 5-butylpyridin-3-yl group, 6-butylpyridin-3-yl group, 2-tert-butylpyridin-3-yl group, 4-tert-butylpyridin-3-yl group, 5-tert-butylpyridin-3-yl group, 6-tert-butylpyridin-3-yl group, 4-pyridyl group, 2-methylpyridin-4-yl group, 3-methylpyridin-4-yl group, 2-ethylpyridin-4-yl group, 3-ethylpyridin-4-yl group, 2-propylpyridin-4-yl group, 3-propylpyridin-4-yl group, 2-butylpyridin-4-yl group, 3-butylpyridin-4-yl group, 2-tert-butylpyridin-4-yl group, 3-tert-butylpyridin-4-yl group and the like can be exemplified.

From the viewpoint of good performance as the material for organic electroluminescence device, phenyl group, p-tolyl group, m-tolyl group, 2-tert-butylphenyl group, 3-tert-butylphenyl group, 4-tert-butylphenyl group, 2,4-di-tert-butylphenyl group, 3,5-di-tert-butylphenyl group, 2-pyridyl group, 3-tert-butylpyridin-2-yl group, 4-tert-butylpyridin-2-yl group, 5-tert-butylpyridin-2-yl group, 6-tert-butylpyridin-2-yl group, 3-pyridyl group or 4-pyridyl group is desirable, and phenyl group, p-tolyl group, m-tolyl group, 4-tert-butylphenyl group, 2-pyridyl group, 3-pyridyl group or 4-pyridyl group is further desirable.

It is essential that at least one pyridine ring is present in the substituent group —$(X)_p$—$Ar^2$ consisting of the aforementioned X and $Ar^2$. As the substituent group —$(X)_p$—$Ar^2$, the groups represented by the basal skeletons A-I to A-XXXVIII described in Tables 1, 2 and 3 can be exemplified, though the invention is not restricted thereby.

TABLE 1

Substituent group-$(X)_p$—$Ar^2$

A-I

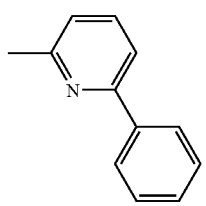

A-II

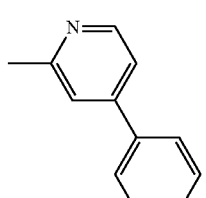

TABLE 1-continued

Substituent group-$(X)_p$—$Ar^2$

A-III

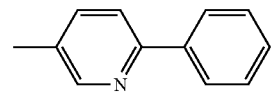

A-IV

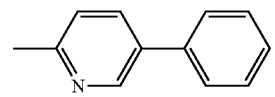

A-V

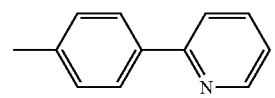

A-VI

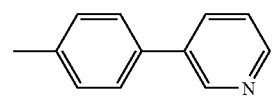

A-VII

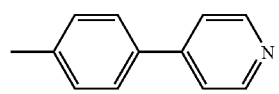

A-VIII

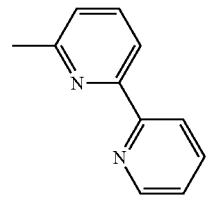

A-IX

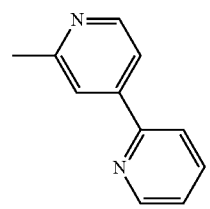

A-X

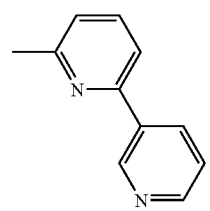

A-XI

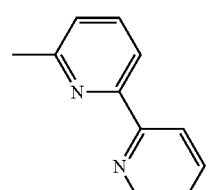

TABLE 1-continued
| Substituent group-(X)$_p$—Ar$^2$ | |
|---|---|
| 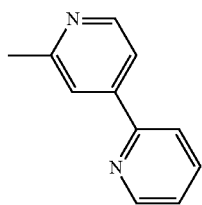 | A-XII |
| 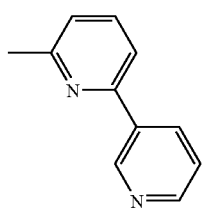 | A-XIII |
| 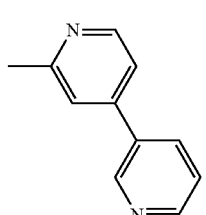 | A-XIV |
| 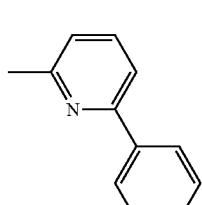 | A-XV |
| 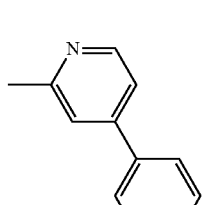 | A-XVI |
TABLE 2
| Substituent group-(X)$_p$—Ar$^2$ | |
|---|---|
| 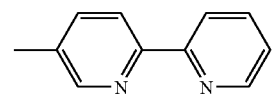 | A-XVII |
| 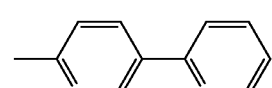 | A-XVIII |
TABLE 2-continued
| Substituent group-(X)$_p$—Ar$^2$ | |
|---|---|
| 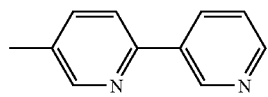 | A-XIX |
| 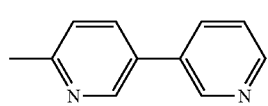 | A-XX |
| 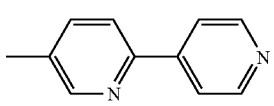 | A-XXI |
| 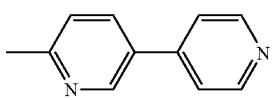 | A-XXII |
| 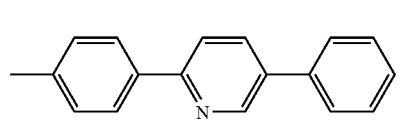 | A-XXIII |
| 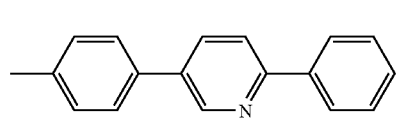 | A-XXIV |
| 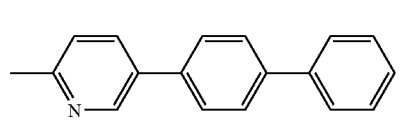 | A-XXV |
| 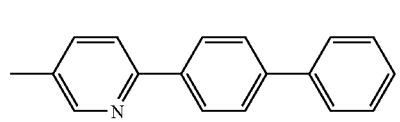 | A-XXVI |
| 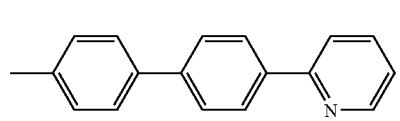 | A-XXVII |
| 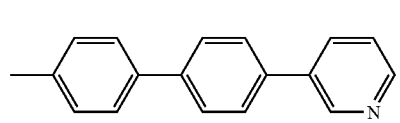 | A-XXVIII |
| 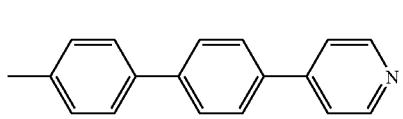 | A-XXIX |
| 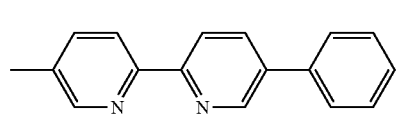 | A-XXX |

TABLE 2-continued

Substituent group-$(X)_p$—$Ar^2$

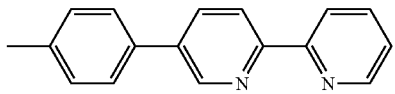
A-XXXI

TABLE 3

Substituent group-$(X)_p$—$Ar^2$

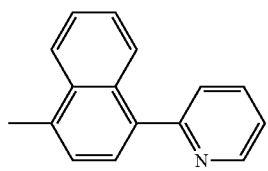
A-XXXII

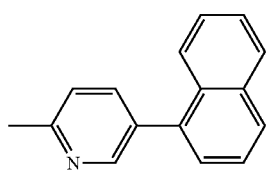
A-XXXIII

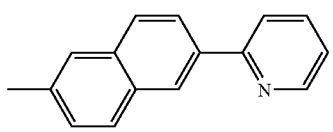
A-XXXIV

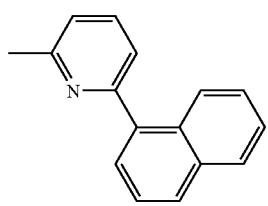
A-XXXV

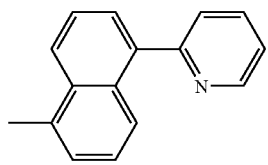
A-XXXVI

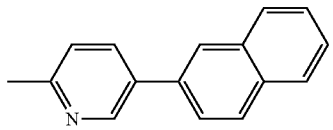
A-XXXVII

TABLE 3-continued

Substituent group-$(X)_p$—$Ar^2$

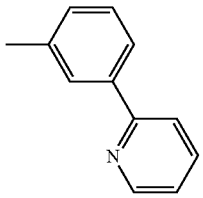
A-XXXVIII

The 1,3,5-triazine derivatives represented by the formula (1) may be the compound consisting of every combination of the above $Ar^1$, a, $R^1$, $R^2$, $R^3$, m, X, p, $Ar^2$ and b, but from the viewpoint of good performance as the material for organic electroluminescence device, 2,4-bis(4-tert-butylphenyl)-6-[4'-(2-pyridyl)biphenyl-4-yl]-1,3,5-triazine, 2-[4-(6-phenylpyridin-2-yl)phenyl]-4,6-di-m-tolyl-1,3,5-triazine, 2-[4-(5-phenylpyridin-2-yl)phenyl]-4,6-di-m-tolyl-1,3,5-triazine, 2-[4'-(2-pyridyl)biphenyl-4-yl]-4,6-di-m-tolyl-1,3,5-triazine, 2,4-bis(4-tert-butylphenyl)-6-[4-(5-phenylpyridin-2-yl)phenyl]-1,3,5-triazine, 2-{4-[5-(4-tert-butylphenyl)pyridin-2-yl]phenyl}-4,6-di-m-tolyl-1,3,5-triazine and the like are desirable.

Also, 6-{4-[4,6-bis(4-tert-butylphenyl)-1,3,5-triazin-2-yl]phenyl}-2,2'-bipyridyl, 5-{4-[4,6-bis(4-tert-butylphenyl)-1,3,5-triazin-2-yl]phenyl}-2,2'-bipyridyl, 2,4-bis(4-tert-butylphenyl)-6-[4'-(5-phenylpyridin-2-yl)biphenyl-4-yl]-1,3,5-triazine, 2,4-bis(4-tert-butylphenyl)-6-[4''-(2-pyridyl)-1,1':4',1''-terphenyl-4-yl]-1,3,5-triazine, 2,4-bis(4-biphenyl)-6-[4'-(2-pyridyl)biphenyl-4-yl]-1,3,5-triazine, 2,4-bis(1-naphthyl)-6-[4'-(2-pyridyl)biphenyl-4-yl]-1,3,5-triazine, 6-[4-(4,6-di-m-tolyl-1,3,5-triazin-2-yl)phenyl]-2,2'-bipyridyl, 6-{4-[4,6-bis-(4-biphenylyl)-1,3,5-triazin-2-yl]phenyl}-2,2'-bipyridyl and the like are desirable.

Also, 2,4-bis(4-tert-butylphenyl)-6-[4'-(3-pyridyl)biphenyl-4-yl]-1,3,5-triazine, 2,4-bis(4-biphenylyl)-6-[3'-(2-pyridyl)biphenyl-4-yl]-1,3,5-triazine, 4-{4-[4,6-bis(4-biphenylyl)-1,3,5-triazin-2-yl]phenyl}-2,2'-bipyridyl, 2-(4-biphenylyl)-4,6-bis[4'-(2-pyridyl)biphenyl-4-yl]-1,3,5-triazine, 5-{4-[4,6-bis(4-tert-butylphenyl)-1,3,5-triazin-2-yl]phenyl}-2,4'-bipyridyl, 5-{4-[4,6-bis(4-biphenylyl)-1,3,5-triazin-2-yl]phenyl}-2,4'-bipyridyl, 2,4-bis(4-biphenylyl)-6-[4'-(3-pyridyl)biphenyl-4-yl]-1,3,5-triazine, 2,4-bis(4-biphenylyl)-6-[4'-(4-pyridyl)biphenyl-4-yl]-1,3,5-triazine and the like are desirable.

Next, the production methods of the invention are described. The 1,3,5-triazine derivatives of the invention can be produced by the following "Production method-A" or "Production method-B".

The "Production method-A" consists of "Step A-1" and "Step A-2".

"Production Method-A"

"Step A-1"

[Chem 6]

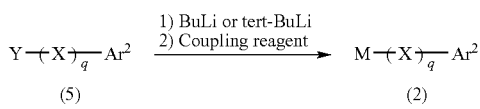

[In the formula, Y, X, q, Ar² and M are as defined in the foregoing.]

"Step A-2"

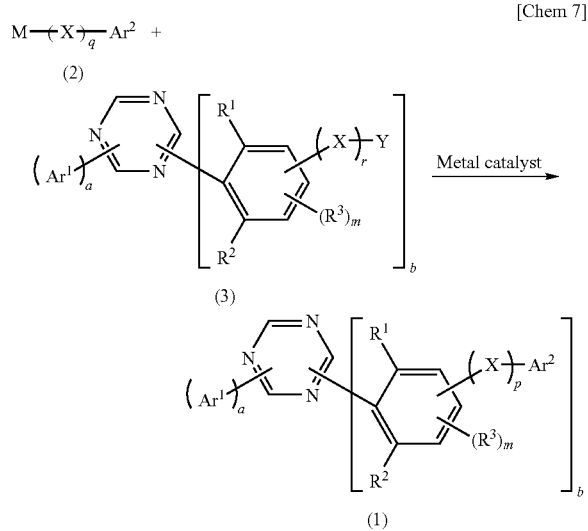

[In the formula, M, X, q, Ar², Ar¹, a, R¹, R², R³, m, r, Y, b and p are as defined in the foregoing.]

Firstly, a substituted aromatic compound which is a reaction species generally used in the coupling reaction, represented by the formula (2), is obtained by the "Step A-1" by lithiating an aromatic compound represented by the formula (5) with butyl lithium, tert-butyl lithium or the like and then allowing it to undergo the reaction with a coupling reagent.

As the coupling reagent, dichloro(tetramethylethylenediamine)zinc(II), zinc chloride, zinc bromide, zinc iodide, trimethyltin chloride, tributyltin chloride, tributyltin hydride, hexamethyldistannane, hexabutyldistannane, boric acid, (2,3-dimethylbutane-2,3-dioxy)borane, ethylenedioxyborane, 1,3-propanedioxyborane, bis(2,3-dimethylbutane-2,3-dioxy)diborane, 1,2-phenylenedioxyborane, trimethoxysilane, triethoxysilane, diethylsilane dichloride and the like can be exemplified, and the compound represented by the formula (2), in which M is a —ZnCl species, a —ZnBr species, a —ZnI species, a —SnMe₃ species, a —SnBu₃ species, a —B(OH)₂ species, a —B(2,3-dimethylbutane-2,3-dioxy) species, a —B(ethylenedioxy) species, a —B(1,3-propanedioxy) species, a —B(1,2-phenylenedioxy) species, a —Si(OMe)₃ species, a —Si(OEt)₃ species or a —SiEtCl₂ species, can be obtained by the reaction with these.

When allowed to react with boric acid, M may be made into a —BF₃⁻K⁺ species, a —BF₃⁻Cs⁺ species, a —BF₃⁻NBu₄⁺ species or the like salt after the reaction by allowing to react with hydrogen fluoride aqueous solution and treating with potassium carbonate, cesium carbonate, tetrabutylammonium fluoride or the like. Also, a substituted aromatic compound (2) in which M is a —MgBr or the like species can also be obtained by allowing the aromatic compound (5) to react directly with magnesium bromide, isopropyl magnesium bromide or the like without carrying out lithiation. Regarding a substituted aromatic compound (2) in which boron is contained in M, a commercially available product can also be used as such. In addition, it can be produced by the method which does not carry out lithiation, described in Journal of Organic Chemistry, vol. 60, 7508-7510, 1995.

Thus obtained these substituted aromatic compounds (2) may be isolated after the reaction or subjected to the next "Step A-2" without isolation. From the viewpoint of good yield, it is desirable to obtain a substituted aromatic compound (2) in which M is a —ZnCl species, a —ZnBr species, a —ZnI species, a —SnMe₃ species or a —SnBu₃ species by allowing, after the lithiation, to react with dichloro(tetramethylethylenediamine)zinc(II), zinc chloride, zinc bromide, zinc iodide, trimethyltin chloride or tributyltin chloride and subject it to the "Step A-2" without isolation, or to use a commercially available compound of a —B(OH)₂ species. It is further desirable to obtain a substituted aromatic compound (2) in which M is a —ZnCl species or a —SnMe₃ species by allowing, after the lithiation, to react with dichloro(tetramethylethylenediamine)zinc(II) or trimethyltin chloride and subject it to the "Step A-2" without isolation, or to use a commercially available compound of a —B(OH)₂ species.

As the leaving group represented by Y, chlorine atom, bromine atom, iodine atom, trifluoromethylsulfonyloxy group and the like can be exemplified, but bromine atom or iodine atom is desirable in view of the good yield.

By the "Step A-2", the 1,3,5-triazine derivative of the invention represented by the formula (1) can be obtained by allowing the substituted aromatic compound represented by the formula (2) obtained in the "Step A-1" to react with a 1,3,5-triazine compound represented by the formula (3) in the presence of a metal catalyst.

As the metal catalyst which can be used in the "Step A-2", for example, a palladium catalyst, a nickel catalyst, an iron catalyst, a ruthenium catalyst, a platinum catalyst, a rhodium catalyst, an iridium catalyst, an osmium catalyst, a cobalt catalyst and the like can be exemplified. As such metal catalysts, a metal, a supported metal, a metal salt such as chloride, bromide, iodide, nitrate, sulfate, carbonate, oxalate or acetate or oxide of a metal, and an olefin complex, a phosphine complex, an amine complex, an ammine complex, an acetylacetonato complex or the like complex compound can be used. In addition, these metals, metal salts and complex compounds can also be used in combination with a tertiary phosphine ligand. From the viewpoint of good yield, a palladium catalyst, an iron catalyst or a nickel catalyst is desirable and a palladium catalyst is further desirable.

As the palladium catalyst, further illustratively, palladium black, palladium sponge and the like palladium metals can be exemplified, and palladium/alumina, palladium/carbon, palladium/silica, palladium/Y-type zeolite, palladium/A-type zeolite, palladium/X-type zeolite, palladium/mordenite, palladium/ZSM-5 and the like supported palladium metals can be exemplified. Also, palladium chloride, palladium bromide, palladium iodide, palladium acetate, palladium trifluoroacetate, palladium nitrate, palladium oxide, palladium sulfate, palladium cyanate, sodium hexachloropalladate, potassium hexachloropalladate, disodium tetrachloropalladate, dipotassium tetrachloropalladate, dipotassium tetrabromopalladate, diammonium tetrachloropalladate, tetraammonium hexachloropalladate and the like metal salts can also be exemplified.

In addition, π-allyl palladium chloride diner, palladium acetylacetonato, tetra(acetonitrile)palladium borofluoride, dichlorobis(acetonitrile)palladium, dichlorobis(benzonitrile)palladium, bis(dibenzylideneacetone)palladium, tris(dibenzylideneacetone)dipalladium, dichlorodiamminepalladium, tetraamminepalladium nitrate, tetraamminepalladium tetrachloropalladate, dichlorodipyridinepalladium, dichloro(2,2'-bipyridyl)palladium, dichloro(phenanthroline)palladium, (tetramethylphenanthroline)palladium nitrate, diphenanthrolinepalladium nitrate, bis(tetramethylphenanthroline)palladium nitrate, dichlorobis(triphenylphosphine)palladium, dichlorobis(tricyclohexylphosphine)palladium, tetrakis (triphenylphosphine)palladium, dichloro[1,2-bis(diphenylphosphino)ethane]palladium, dichloro[1,3-bis(diphenylphosphino)propane]palladium, dichloro[1,4-bis (diphenylphosphino)butane]palladium, dichloro[1,1'-bis (diphenylphosphino)ferrocenepalladium and the like complex compounds can also be exemplified.

The palladium catalyst to be used in the "Step A-2" may be any one of the aforementioned metals, supported metals, metal salts and complex compound, but from the viewpoint of good yield, palladium chloride, palladium acetate, π-allyl palladium chloride dimer, bis(dibenzylideneacetone)palladium, tris(dibenzylideneacetone)dipalladium, dichlorobis (triphenylphosphine)palladium, tetrakis(triphenylphosphine)palladium, dichloro[1,2-bis(diphenylphosphino) ethane]palladium, dichloro[1,3-bis(diphenylphosphino) propane]palladium, dichloro[1,4-bis(diphenylphosphino) butane]palladium, dichloro[1,1'-bis(diphenylphosphino) ferrocenepalladium, palladium/alumina and palladium/ carbon are desirable and tetrakis(triphenylphosphine) palladium is further desirable.

These palladium catalyst may be used alone, may also be used in combination with a tertiary phosphine. As the tertiary phosphine which can be used, triphenylphosphine, trimethylphosphine, triethylphosphine, tripropylphosphine, triisopropylphosphine, tributylphosphine, triisobutylphosphine, tri-tert-butylphosphine, trineopentylphosphine, tricyclohexylphosphine, trioctylphosphine, tris(hydroxymethyl) phosphine, tris(2-hydroxyethyl)phosphine, tris(3-hydroxypropyl)phosphine, tris(2-cyanoethyl)phosphine, (+)-1,2-bis [(2R,5R)-2,5-diethylphosphorano]ethane, triallylphosphine, triamylphosphine, tricyclohexyldiphenylphosphine, methyldiphenylphosphine and the like can be exemplified.

Also, ethyldiphenylphosphine, propyldiphenylphosphine, isopropyldiphenylphosphine, butyldiphenylphosphine, isobutyldiphenylphosphine, tert-butyldiphenylphosphine, 9,9-dimethyl-4,5-bis(diphenylphosphino)xanthene, 2-(diphenylphosphino)-2'-(N,N-dimethylamino)biphenyl, (R)-(+)-2-(diphenylphosphino)-2'-methoxy-1,1'-binaphthyl, (−)-1,2-bis[(2R,5R)-2,5-dimethylphosphorano]benzene, (+)-1,2-bis[(2S,5S)-2,5-dimethylphosphorano]benzene, (−)-1,2-bis[(2R,5R)-2,5-diethylphosphorano]benzene, (+)-1,2-bis[(2S,5S)-2,5-diethylphosphorano]benzene, and the like can be exemplified.

Also, 1,1'-bis(diisopropylphosphino)ferrocene, (−)-1,1'-bis[(2S,4S)-2,4-diethylphosphorano]ferrocene, (R)-(−)-1-[(S)-2-(dicyclohexylphosphino)ferrocenyl]ethyl-dicyclohexylphosphine, (+)-1,2-bis[(2R,5R)-2,5-diisopropylphosphorano]benzene, (−)-1,2-bis[(2S,5S)-2,5-diisopropylphosphorano]benzene, (±)-2-(di-tert-butylphosphino)-1,1'-binaphthyl, 2-(di-tert-butylphosphino) biphenyl, 2-(dicyclohexylphosphino)biphenyl, 2-(dicyclohexylphosphino)-2'-methylbiphenyl, bis(diphenylphosphino)methane, 1,2-bis(diphenylphosphino)ethane and the like can be exemplified.

Also, 1,2-bis(dipentafluorophenylphosphino)ethane, 1,3-bis(diphenylphosphino)propane, 1,4-bis(diphenylphosphino)butane, 1,4-bis(diphenylphosphino)pentane, 1,1'-bis (diphenylphosphino)ferrocene, (2R,3R)-(−)-2,3-bis (diphenylphosphino)-bicyclo[2.2.1]hepta-5-ene, (2S,3S)-(+)-2,3-bis(diphenylphosphino)-bicyclo[2.2.1]hepta-5-ene, (2S,3S)-(−)-bis(diphenylphosphino)butane, cis-1,2-bis (diphenylphosphino)ethylene, bis(2-diphenylphosphinoethyl)phenylphosphine, (2S,4S)-(−)-2,4-1,4-bis(diphenylphosphino)pentane, (2R,4R)-(−)-2,4-1,4-bis (diphenylphosphino)pentane and the like can be exemplified.

Also, R-(+)-1,2-bis(diphenylphosphino)propane, (2S,3S)-(+)-1,4-bis(diphenylphosphino)-2,3-O-isopropylidene-2,3-butanediol, tri(2-furyl)phosphine, tri(1-naphthyl)phosphine, tris[3,5-bis(trifluoromethyl)phenyl]phosphine, tris(3-chlorophenyl)phosphine, tris(4-chlorophenyl)phosphine, tris(3,5-dimethylphenyl)phosphine, tris(3-fluorophenyl)phosphine, tris(4-fluorophenyl)phosphine, tris(2-methoxyphenyl) phosphine, tris(3-methoxyphenyl)phosphine, tris(4-methoxyphenyl)phosphine, tris(2,4,6-trimethoxyphenyl) phosphine and the like can be exemplified.

Also, tris(pentafluorophenyl)phosphine, tris[4-(perfluorohexyl)phenyl]phosphine, tris(2-thienyl)phosphine, tris(m-tolyl)phosphine, tris(o-tolyl)phosphine, tris(p-tolyl)phosphine, tris(4-trifluoromethylphenyl)phosphine, tri(2,5-xylyl) phosphine, tri(3,5-xylyl)phosphine, 1,2-bis (diphenylphosphino)benzene, (R)-(+)-2,2'-bis (diphenylphosphino)-1,1'-binaphthyl, (S)-(−)-2,2'-bis (diphenylphosphino)-1,1'-binaphthyl, (+)-2,2'-bis (diphenylphosphino)-1,1'-binaphthyl, 2,2'-bis (diphenylphosphino)-1,1'-biphenyl, (S)-(+)-4,12-bis (diphenylphosphino)-[2.2]-paracyclophane and the like can be exemplified.

Also, (R)-(−)-4,12-bis(diphenylphosphino)-[2.2]-paracyclophane, (R)-(+)-2,2'-bis(di-p-tolylphosphino)-1,1'-binaphthyl, (S)-(−)-2,2'-bis(di-p-tolylphosphino)-1,1'-binaphthyl, bis(2-methoxyphenyl)phenylphosphine, 1,2-bis(diphenylphosphino)benzene, (1R,2R)-(+)-N,N'-bis(2'-diphenylphosphinobenzoyl)-1,2-diaminocyclohexane, (1S,2S)-(+)-N,N'-bis(2'-diphenylphosphinobenzoyl)-1,2-diaminocyclohexane, (±)—N,N'-bis(2'-diphenylphosphinobenzoyl)-1,2-diaminocyclohexane, (1S, 2S)-(−)-N,N'-bis(2-diphenylphosphino-1-naphthoyl)-1,2-diaminocyclohexane and the like can be exemplified.

In addition, (1R,2R)-(+)-N,N'-bis(2-diphenylphosphino-1-naphthoyl)-1,2-diaminocyclohexane, (±)-N,N'-bis(2-diphenylphosphino-1-naphthoyl)diaminocyclohexane, tris (diethylamino)phosphine, bis(diphenylphosphino)acetylene, bis(2-diphenylphosphinophenyl)ether, (R)-(−)-1-[(S)-2-(dicyclohexylphosphino)ferrocenyl]ethyldiphenylphosphine, (R)-(−)-1-[(S)-2-(diphenylphosphino)ferrocenyl]ethyl-di-tert-butylphosphine, bis(p-sulfonatophenyl)phenylphosphine dipotassium salt, 2-dicyclohexylphosphino-2'-(N,N-dimethylamino)biphenyl, (S)-(−)-1-(2-diphenylphosphino-1-naphthyl)isoquinoline, tris(trimethylsilyl)phosphine and the like can be exemplified.

The tertiary phosphine to be used may be any one of the aforementioned tertiary phosphines, but in view of the good yield, triphenylphosphine, trimethylphosphine, triethylphosphine, tributylphosphine, tri(tert-butyl)phosphine, tricyclohexylphosphine, trioctylphosphine, 9,9-dimethyl-4,5-bis (diphenylphosphino)xanthene, 2-(di-tert-butylphosphino) biphenyl, 2-(dicyclohexylphosphino)biphenyl, 1,2-bis (diphenylphosphino)ethane, 1,3-bis(diphenylphosphino) propane, 1,4-bis(diphenylphosphino)butane, 1,1'-bis (diphenylphosphino)ferrocene, (R)-(+)-2,2'-bis (diphenylphosphino)-1,1'-binaphthyl, (S)-(−)-2,2'-bis (diphenylphosphino)-1,1'-binaphthyl and (±)-2,2'-bis (diphenylphosphino)-1,1'-binaphthyl are desirable.

Particularly, triphenylphosphine, trimethylphosphine, tributylphosphine, tri(tert-butyl)phosphine, tricyclohexylphosphine, trioctylphosphine, 2-(di-tert-butylphosphino)biphenyl, 2-(dicyclohexylphosphino)biphenyl, 1,2-bis(diphenylphosphino)ethane, 1,3-bis(diphenylphosphino)propane, 1,4-bis(diphenylphosphino)butane, 1,1'-bis(diphenylphosphino)ferrocene, (R)-(+)-2,2'-bis(diphenylphosphino)-1,1'-binaphthyl, (S)-(−)-2,2'-bis(diphenylphosphino)-1,1'-binaphthyl and (±)-2,2'-bis(diphenylphosphino)-1,1'-binaphthyl are further desirable.

In addition, a base may be added in the "Step A-2" for the yield improvement. As the base to be added, lithium carbonate, sodium carbonate, sodium hydrogen carbonate, potassium carbonate, cesium carbonate, potassium fluoride, cesium fluoride, sodium hydroxide, potassium hydroxide, tripotassium phosphate, triethylamine, butylamine, diisopropylamine, ethyldiisopropylamine, potassium-tert-butoxide, sodium-tert-butoxide or the like inorganic base or organic base can be exemplified. The reaction sufficiently progresses without adding the base.

Molar ratio of the butyl lithium or tert-butyl lithium to be used for the lithiation in the "Step A-1" with the aromatic compound (5) is desirably from 1:1 to 5:1, further desirably from 1:1 to 3:1 from the viewpoint of good yield.

As the solvent to be used in the lithiation and the reaction with a coupling reagent in the "Step A-1", tetrahydrofuran, toluene, benzene, diethyl ether, xylene, chloroform, dichloromethane and the like can be exemplified, and these may be used in an optional combination. It is desirable to use tetrahydrofuran alone from the viewpoint of good yield.

Concentration of the aromatic compound (5) in the "Step A-1" is desirably from 10 mmol/L to 1000 mmol/L, further desirably from 50 mmol/L to 200 mmol/L from the viewpoint of good yield.

Reaction temperature in carrying out lithiation in the "Step A-1" is desirably from −150° C. to −20° C., further desirably a temperature optionally selected from −100° C. to −60° C. from the viewpoint of good yield.

Reaction time for the lithiation in the "Step A-1" is desirably from 1 minute to 3 hours, further desirably from 15 minutes to 1 hour from the viewpoint of good yield.

Molar ratio of the coupling reagent with the aromatic compound (5) in the "Step A-1" is desirably from 1:1 to 1:10, further desirably from 1:1.5 to 1:3 from the viewpoint of good yield.

Regarding the reaction temperature after the addition of the coupling reagent in the "Step A-1", it is desirable to increase the temperature from a low temperature range of from −150° C. to −20° C. to a high temperature range of from −20° C. to 50° C., and it is further desirable to increase the temperature from a low temperature range of from −100° C. to −60° C. to a high temperature range of from 0° C. to 30° C., from the viewpoint of good yield.

The period of time for the reaction with the coupling reagent in the "Step A-1" varies depending on the substrate, reaction scale and the like and is not particularly limited, but the reaction at the low temperature range is desirably from 1 minute to 1 hour, further desirably from 5 minutes to 30 minutes from the viewpoint of good yield. The reaction at the high temperature range is desirably from 10 minutes to 10 hours, further desirably from 30 minutes to 5 hours from the viewpoint of good yield.

In the "Step A-2" when 1 equivalent or more of the substituted aromatic compound (2) is allowed to react with the 1,3,5-triazine compound (3) in the case of a 1,3,5-triazine compound (3) wherein a=2 (b=1), a 1,3,5-triazine derivative of the formula (1) wherein a=2 (b=1) can be obtained with a good yield. Also, when 2 equivalents or more of the substituted aromatic compound (2) is allowed to react with the 1,3,5-triazine compound (3) in the case of a 1,3,5-triazine compound (3) wherein a=1 (b=2), a 1,3,5-triazine derivative of the formula (1) wherein a=1 (b=2) can be obtained with a good yield.

Molar ratio of the metal catalyst and the 1,3,5-triazine compound (3) in the "Step A-2" is desirably from 0.001:1 to 0.5:1, further preferably from 0.01:1 to 0.1:1 from the viewpoint of good yield.

As the solvent which can be used in the "Step A-2", methanol, ethanol, isopropyl alcohol, N,N-dimethylformamide, dioxane, diethyl ether, xylene, toluene, benzene, tetrahydrofuran, acetonitrile, dichloromethane, dimethyl sulfoxide, N-methyl-2-pyrrolidone, hexamethyl phosphoric acid triamide, dimethoxyethane and the like can be exemplified, and these may be used in an optional combination. From the viewpoint of good yield, dioxane, diethyl ether, toluene or tetrahydrofuran is desirable. When the substituted aromatic compound (2) formed in the "Step A-1" is subjected to the "Step A-2" without isolation, the solvent used in the "Step A-1" can be used as such.

Concentration of the 1,3,5-triazine compound (3) in the "Step A-2" is desirably from 5 mmol/L to 1000 mmol/L, further desirably from 10 mmol/L to 200 mmol/L from the viewpoint of good yield.

Regarding the reaction temperature in the "Step A-2", it is desirably a temperature optionally selected from 0° C. to reflux temperature of the solvent to be used, and reflux temperature of the solvent is further desirable from the viewpoint of good yield.

Reaction time in the "Step A-2" is desirably from 10 minutes to 48 hours, further desirably from 30 minutes to 24 hours from the viewpoint of good yield.

Next, the "Production method-B" is described. The "Production method-B" consists of "Step B-1" and "Step B-2".

"Production Method-B"

"Step B-1"

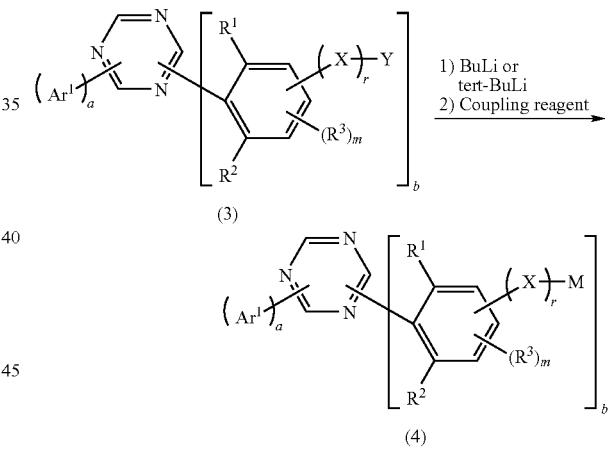

[In the formula, Ar¹, a, R¹, R², R³, m, X, r, Y, b and M are as defined in the foregoing.]

"Step B-2"

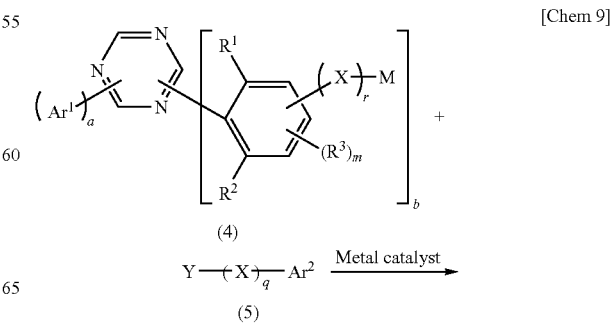

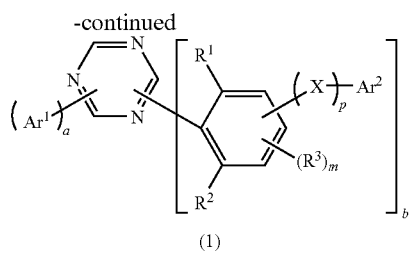

(1)

[In the formula, $Ar^1$, a, $R^1$, $R^2$, $R^3$, m, M, b, Y, X, p, q and $Ar^2$ are as defined in the foregoing.]

Firstly, a substituted 1,3,5-triazine compound (4) which is a reaction species generally used in the coupling reaction is obtained by the "Step B-1" by lithiating a 1,3,5-triazine compound (3) with butyl lithium, tert-butyl lithium or the like and then allowing it to undergo the reaction with a coupling reagent. As the coupling reagent, dichloro(tetramethylethylenediamine)zinc(II), zinc chloride, zinc bromide, zinc iodide, trimethyltin chloride, tributyltin chloride, tributyltin hydride, hexamethyldistannane, hexabutyldistannane, boric acid, (2,3-dimethylbutane-2,3-dioxy)borane, ethylenedioxyborane, 1,3-propanedioxyborane, bis(2,3-dimethylbutane-2,3-dioxy)diborane, 1,2-phenylenedioxyborane, trimethoxysilane, triethoxysilane, diethylsilane dichloride and the like, which were exemplified in the "Step A-1", can be exemplified, and the substituted 1,3,5-triazine compound (4), in which $M^2$ is a —ZnCl species, a —ZnBr species, a —ZnI species, a —SnMe$_3$ species, a —SnBu$_3$ species, a —B(OH)$_2$ species, a —B(2,3-dimethylbutane-2,3-dioxy) species, a —B(ethylenedioxy) species, a —B(1,3-propanedioxy) species, a —B(1,2-phenylenedioxy) species, a —Si(OMe)$_3$ species, a —Si(OEt)$_3$ species or a —SiEtCl$_2$ species, can be obtained by the reaction with these.

When allowed to react with boric acid, $M^2$ may be made into a —BF$_3^-$K$^+$ species, a —BF$_3^-$Cs$^+$ species, a —BF$_3^-$NBu$_4^+$ species or the like salt after the reaction by allowing to react with hydrogen fluoride aqueous solution and treating with potassium carbonate, cesium carbonate, tetrabutylammonium fluoride or the like. Also, a compound (4) in which $M^2$ is a —MgBr or the like species can also be obtained by allowing the 1,3,5-triazine compound (3) to react directly with magnesium bromide, isopropyl magnesium bromide or the like without carrying out lithiation. Regarding a substituted 1,3,5-triazine compound (4) in which boron is contained in M, it can be produced by the method which does not carry out lithiation, described in Journal of Organic Chemistry, vol. 60, 7508-7510, 1995. A commercially available product can also be used as such.

Thus obtained these substituted 1,3,5-triazine compounds (4) may be isolated after the reaction or subjected to the next "Step B-2" without isolation. From the viewpoint of good yield, it is desirable to obtain a substituted 1,3,5-triazine compound (4) in which M is a ZnCl species, a —ZnBr species, a —ZnI species, a —SnMe$_3$ species or a —SnBu$_3$ species by allowing, after the lithiation, to react with dichloro(tetramethylethylenediamine)zinc(II), zinc chloride, zinc bromide, zinc iodide, trimethyltin chloride or tributyltin chloride and subject it to the "Step B-2" without isolation. It is further desirable to obtain a substituted 1,3,5-triazine compound (4) in which M is a —ZnCl species or a —SnMe$_3$ species by allowing, after the lithiation, to react with dichloro(tetramethylethylenediamine)zinc(II) or trimethyltin chloride and subject it to the "Step B-2" without isolation.

In the "Step B-2", the 1,3,5-triazine derivative of the invention represented by the formula (1) is obtained by allowing the substituted 1,3,5-triazine compound (4) obtained in the "Step B-1" to react with an aromatic compound (5) in the presence of a metal catalyst.

As the metal catalyst which can be used in the "Step B-2", a palladium catalyst, a nickel catalyst, an iron catalyst, a ruthenium catalyst, a platinum catalyst, a rhodium catalyst, an iridium catalyst, an osmium catalyst, a cobalt catalyst and the like, exemplified in the "Step A-2", can be exemplified. As such metal catalysts, a metal, a metal salt such as chloride, bromide, iodide, nitrate, sulfate, carbonate, oxalate or acetate or oxide of a metal, and an olefin complex, a phosphine complex, an amine complex, an ammine complex, an acetylacetonato complex or the like complex compound can be used. In addition, these metals, metal salts and complex compounds can also be used in combination with a tertiary phosphine ligand. From the viewpoint of good yield, a palladium catalyst, an iron catalyst or a nickel catalyst is desirable and a palladium catalyst is further desirable.

As the palladium catalyst, further illustratively, palladium black and the like metals, palladium/alumina, palladium/carbon and the like supported metals, palladium chloride, palladium acetate and the like metal salts, π-allyl palladium chloride dimer, bis(dibenzylideneacetone)palladium, tris(dibenzylideneacetone)dipalladium, dichlorobis(triphenylphosphine)palladium, tetrakis(triphenylphosphine)palladium, dichloro[1,2-bis(diphenylphosphino)ethane]palladium, dichloro[1,3-bis(diphenylphosphino)propane]palladium, dichloro[1,4-bis(diphenylphosphino)butane]palladium, dichloro[1,1'-bis(diphenylphosphino)ferrocenepalladium and the like complex compounds, exemplified in the "Step A-2", can also be exemplified. From the viewpoint of good yield, tetrakis(triphenylphosphine)palladium is desirable.

These metals, supported metals, metal salts and complex compounds may be used alone but may also be used in combination with a tertiary phosphine ligand. As the tertiary phosphine which can be used, triphenylphosphine, trimethylphosphine, triethylphosphine, tributylphosphine, tri(tert-butyl)phosphine, tricyclohexylphosphine, trioctylphosphine, 9,9-dimethyl-4,5-bis(diphenylphosphino)xanthene, 2-(di-tert-butylphosphino)biphenyl, 2-(dicyclohexylphosphino)biphenyl, 1,2-bis(diphenylphosphino)ethane, 1,3-bis(diphenylphosphino)propane, 1,4-bis(diphenylphosphino)butane, 1,1'-bis(diphenylphosphino)ferrocene, (R)-(+)-2,2'-bis(diphenylphosphino)-1,1'-binaphthyl, (S)-(−)-2,2'-bis(diphenylphosphino)-1,1'-binaphthyl and (±)-2,2'-bis(diphenylphosphino)-1,1'-binaphthyl and the like, exemplified in the "Step A-2", can be exemplified.

In addition, a base may be added in the "Step B-2" for the yield improvement. As the base to be added, lithium carbonate, sodium carbonate, sodium hydrogen carbonate, potassium carbonate, cesium carbonate, potassium fluoride, cesium fluoride, sodium hydroxide, potassium hydroxide, tripotassium phosphate, triethylamine, butylamine, diisopropylamine, ethyldiisopropylamine, potassium-tert-butoxide, sodium-tert-butoxide or the like inorganic base or organic base can be exemplified. The reaction sufficiently progresses without adding the base.

Molar ratio of the butyl lithium or tert-butyl lithium to be used for the lithiation in the "Step B-1" with the 1,3,5-triazine compound (3) is desirably from 2:1 to 5:1, further desirably from 2:1 to 3:1 from the viewpoint of good yield.

As the solvent to be used in the lithiation and the reaction with a coupling reagent in the "Step B-1", tetrahydrofuran, toluene, benzene, diethyl ether, xylene, chloroform, dichloromethane and the like can be exemplified, and these may be used in an optional combination. It is desirable to use tetrahydrofuran alone from the viewpoint of good yield.

Concentration of the 1,3,5-triazine compound (3) in the "Step B-1" is desirably from 5 mmol/L to 1000 mmol/L, further desirably from 10 mmol/L to 200 mmol/L from the viewpoint of good yield.

Reaction temperature in carrying out lithiation in the "Step B-1" is desirably from −150° C. to −20° C., further desirably a temperature optionally selected from −100° C. to −60° C. from the viewpoint of good yield.

Reaction time for the lithiation in the "Step B-1" is desirably from 1 minute to 3 hours, further desirably from 5 minutes to 1 hour from the viewpoint of good yield.

Molar ratio of the coupling reagent with the 1,3,5-triazine compound (3) in the "Step B-1" is desirably from to 10:1, further desirably from 2:1 to 3:1 from the viewpoint of good yield.

Regarding the reaction temperature after the addition of the coupling reagent in the "Step B-1", it is desirable to increase the temperature from a low temperature range of from −150° C. to −20° C. to a high temperature range of from −20° C. to 50° C., and it is further desirable to increase the temperature from a low temperature range of from −100° C. to −60° C. to a high temperature range of from 0° C. to 30° C., from the viewpoint of good yield.

The period of time for the reaction with the coupling reagent in the "Step B-1" varies depending on the substrate, reaction scale and the like and is not particularly limited, but the reaction at the low temperature range is desirably from 1 minute to 3 hour, further desirably from 5 minutes to 1 hour from the viewpoint of good yield. The reaction at the high temperature range is desirably from 10 minutes to 10 hours, further desirably from 30 minutes to 5 hours from the viewpoint of good yield.

In the "Step B-2", when 2 equivalents or more of the aromatic compound (5) is allowed to react with the substituted 1,3,5-triazine compound (4), the 1,3,5-triazine derivative of the formula (1) can be obtained with a good yield.

Molar ratio of the metal catalyst and the aromatic compound (5) in the "Step B-2" is desirably from 0.001:1 to 0.5:1, further preferably from 0.01:1 to 0.1:1 from the viewpoint of good yield.

As the solvent which can be used in the "Step B-2", methanol, ethanol, isopropyl alcohol, N,N-dimethylformamide, dioxane, diethyl ether, xylene, toluene, benzene, tetrahydrofuran, acetonitrile, dichloromethane, dimethyl sulfoxide, N-methyl-2-pyrrolidone, hexamethyl phosphoric acid triamide, dimethoxyethane and the like can be exemplified, and these may be used in an optional combination. From the viewpoint of good yield, dioxane, diethyl ether, toluene or tetrahydrofuran is desirable. From the viewpoint of good yield, it is further desirable to subject the substituted 1,3,5-triazine compound (4) formed in the "Step B-1" to the "Step B-2" without isolation, and in that case, the tetrahydrofuran used in the "Step B-1" can also be used as such.

Concentration of the aromatic compound (5) in the "Step B-2" is desirably from 5 mmol/L to 1000 mmol/L, further desirably from 10 mmol/L to 200 mmol/L from the viewpoint of good yield.

Regarding the reaction temperature in the "Step B-2", it is desirably a temperature optionally selected from 0° C. to reflux temperature of the solvent to be used, and reflux temperature of the solvent is further desirable from the viewpoint of good yield.

Reaction time in the "Step B-2" is desirably from 1 hour to 120 hours, further desirably from 6 hours to 72 hours from the viewpoint of good yield.

Crude product of the 1,3,5-triazine derivative represented by the formula (1) is obtained by evaporating the solvent after completion of the "Step A-2" or "Step B-2". As the purification method of the crude product, recrystallization, column purification, sublimation and the like can be exemplified. For example, in the recrystallization, it can be easily purified by either one of a method in which it is dissolved in a good solvent or a combination of a good solvent and a poor solvent and cooled or a method in which it is dissolved in a good solvent and a poor solvent is added thereto. Though it depends on the solubility of the crude product, a method in which it is dissolved in dichloromethane and then methanol is added thereto is desirable. When a column purification is carried out, it is desirable to use silica gel. As the eluting solution, a hexane-dichloromethane or hexane-chloroform combination is desirable from the viewpoint of good yield. It can be optionally selected within the range of from 1:0 to 0:1 as the volume ratio of hexane and dichloromethane or hexane and chloroform, in response to the degree of separation and elution. In addition, their ratio may be optionally changed during the purification.

The aromatic compound represented by the formula (5) can be easily obtained using Y—X—Y, Y—(X)$_p$—Y, Y—Ar$^2$, Y—X—Ar$^2$ or the like by the coupling reaction which uses a general metal catalyst described, for example, in "Palladium Reagents and Catalysts", edited by J. Tsuji, John Wiley & Sons, Ltd, West Sussex, 2004. In that case, the catalysts, solvents and reaction conditions exemplified in the "Step A-2" or "Step B-2" can be employed. In addition, an aromatic compound (5) in which Y is bromine atom can also be obtained easily by the method described in Journal of Organic Chemistry, vol. 68, 2028-2029, 2003.

That is, it can also be obtained by lithiating an aromatic compound represented by formula (6):

[Chem 10]

$$H{\rm-\!\!\!+\!\!\!X\!\!\!\rightarrow}_{q}{\rm Ar}^2 \tag{6}$$

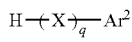

[in the formula, X, q and Ar$^2$ are as defined in the foregoing] with butyl lithium in the presence of 2-dimethylaminoethoxyethanol and then allowing to react with carbon tetrabromide.

Regarding the synthesizing method of the 1,3,5-triazine compound represented by the formula (3), the method described in JP-A-2006-62962 can for example be used.

That is, a 1,3,5-triazine compound of formula (3) in which a=2 (b=1) can be obtained by allowing a substituted benzoyl chloride derivative represented by formula (7):

[Chem 11]

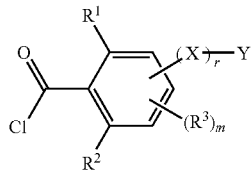

(7)

[in the formula, R$^1$, R$^2$, R$^3$, m, X, r and Y are as described in the foregoing] and a substituted benzonitrile derivative represented by formula (8):
[Chem 12]

$$\text{Ar}^1{\rm-\!\!\!CN} \tag{8}$$

[in the formula, Ar$^1$ is as described in the foregoing] to undergo the reaction in the presence of a Lewis acid to obtain a 1,3,5-oxadianil-1-ium derivative represented by formula (9):

[Chem 13]

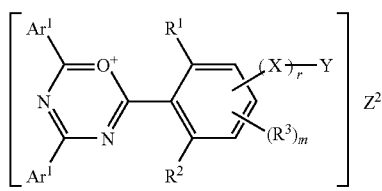

[in the formula, $Ar^1$, $Ar^2$, $R^1$, $R^2$, $R^3$, m, X, r and Y are as defined in the foregoing, and $Z^2$ represents an anion], and treating this with aqueous ammonia.

Also, a 1,3,5-triazine compound of formula (3) in which a=1 (b=2) can be obtained by allowing a substituted benzoyl chloride derivative represented by formula (10):

[Chem 14]

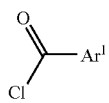

[in the formula, $Ar^1$ is as described in the foregoing] and a substituted benzonitrile derivative represented by formula (11):

[Chem 15]

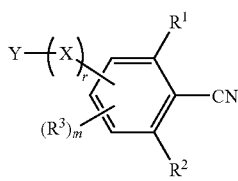

[in the formula, $R^1$, $R^2$, $R^3$, m, Y, X and r are as described in the foregoing] to undergo the reaction in the presence of a Lewis acid to obtain a 1,3,5-oxadianil-1-ium derivative represented by formula (12)

[Chem 16]

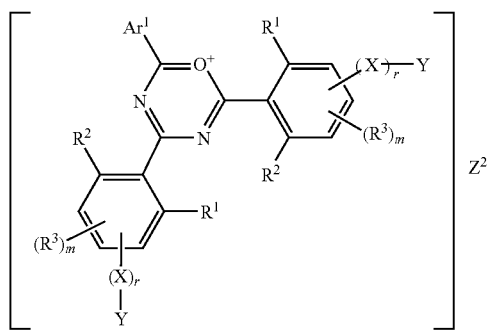

and treating this with aqueous ammonia.

Regarding molar ratio of the benzoyl chloride derivatives represented by the formulae (7) and (10) and the benzonitrile derivatives represented by the formulae (8) and (11), either one may be in an excess amount, but the reaction sufficiently progresses even by a stoichiometric amount.

As the solvent to be used in the reaction, for example, chloroform, dichloromethane, 1,2-dichloroethane, 1,1,2,2-tetrachloroethane, carbon tetrachloride, chlorobenzene, 1,2-dichlorobenzene and the like can be cited. Dichloromethane or chloroform is desirable from the viewpoint of good yield.

As the Lewis acid, boron trifluoride, aluminum trichloride, ferric chloride, stannic chloride, antimony pentachloride and the like can be exemplified. From the viewpoint of good yield, antimony pentachloride is desirable.

Salt of the formula (9) or (12) can be isolated, but may be subjected to the subsequent reaction operation directly as the solution. In the case of isolating as a salt, $Z^2$ of the formula (9) or (12) is not particularly limited with the proviso that it is an anion, but the yield becomes good when tetrafluoroborate ion, chlorotrifluoroborate ion, tetrachloroaluminate ion, tetrachloroferrate(III) ion, pentachlorostannate(IV) ion or hexachloroantimonite(V) ion, in which fluoride ion or chloride ion is linked to the aforementioned Lewis acids, is obtained as the counter anion.

Though concentration of aqueous ammonia to be used is not particularly limited, from 5 to 50% is desirable, and the reaction sufficiently progresses even by the commercially available 28% product.

Though the reaction temperature is not particularly limited, it is desirable to carry out the reaction at a temperature optionally selected from −50° C. to solvent reflux temperature. In addition, the reaction time is from 30 minutes to 24 hours though it depends on the equilibrium with the reaction temperature.

The production method of a thin film for the organic electroluminescence device comprising the 1,3,5-triazine derivative represented by the formula (1) is not particularly limited, and film formation by a vacuum evaporation method is possible. The film formation by a vacuum evaporation method can be carried out by using a generally used film formation by a vacuum evaporation equipment. Considering the production tact time and production cost for the preparation of the organic electroluminescence device, it is desirable that the degree of vacuum in its vacuum vessel in forming the film by the vacuum evaporation method is approximately from $1 \times 10^{-2}$ to $1 \times 10^{-5}$ Pa which can be attained by generally used diffusion pump, turbo-molecular pump, cryopump and the like. It is desirable that the evaporation rate is from 0.005 to 1.0 nm/second, though it depends on the thickness of the film to be formed. In addition, since the 1,3,5-triazine derivative represented by the formula (1) has high solubility in chloroform, dichloromethane, 1,2-dichloroethane, chlorobenzene, toluene, ethyl acetate, tetrahydrofuran or the like, film formation by a spin coating method, an ink jet method, a casting method, a dipping method or the like using a generally used equipment is also possible.

Since the thin film comprising the 1,3,5-triazine derivative of the invention represented by the formula (1) has high surface smoothness, amorphousness, heat resistance, electron transporting ability, positive hole blocking ability, redox resistance, water resistance, oxygen resistance, luminescence and the like, it is possible to use it as a material of an organic electroluminescence device, particularly, it can be used as an electron transporter, a positive hole blocking material, a luminescent material, a luminescence host material and the like. Accordingly, the thin film comprising the 1,3,5-triazine derivative of the invention represented by the formula (1) can be used as a composing component of an organic electroluminescence device.

The following describes reference examples and examples of the invention, but the invention is not limited to these examples.

Reference Example 1

Synthesis of 2-(4-bromophenyl)-4,6-bis(4-tert-butylphenyl)-1,3,5-triazine

A 6.58 g portion of 4-bromobenzoyl chloride and 9.55 g of 4-tert-butylbenzonitrile were dissolved in 200 mL of chloroform, and 8.97 g of antimony pentachloride was added dropwise thereto at 0° C. The mixture was stirred at room temperature for 1 hour and then refluxed for 8 hours. After cooling to room temperature, chloroform was evaporated under a reduced pressure. When the thus obtained 2-(4-bromophenyl)-4,6-bis(4-tert-butylphenyl)-1,3,5-oxadiazinyl-1-ium hexachloroantimonate was gradually added to 300 ml of 28% aqueous ammonia at 0° C., white precipitate was formed. This was stirred at room temperature for 1 hour and filtered, and then the thus obtained white precipitate was washed with water and methanol. The white precipitate was dried and then dissolved by adding to dimethylformamide heated to 153° C., followed by filtration. The operation to add the insoluble component separated by filtration to dimethylformamide heated to 153° C. and then to filtrate was further carried out three times. By combining and cooling all of the filtrates and again filtrating and drying the thus formed white precipitate, a white solid of 2-(4-bromophenyl)-4,6-bis(4-tert-butylphenyl)-1,3,5-triazine (10.41 g, yield 69%) was obtained.

$^1$H-NMR (CDCl$_3$): δ 1.44 (s, 18H), 7.63 (d, J=8.6 Hz, 4H), 7.73 (d, J=8.6 Hz, 2H), 8.67 (d, J=8.6 Hz, 2H), 8.69 (d, J=8.6 Hz, 4H).

$^{13}$C-NMR (CDCl$_3$): δ 31.2, 35.1, 125.6, 127.2, 128.8, 130.4, 131.8, 133.4, 135.4, 156.2, 170.6, 171.6.

Reference Example 2

Synthesis of 2-(4-bromophenyl)-4,6-di-m-tolyl-1,3,5-triazine

An 8.78 g portion of 4-bromobenzoyl chloride and 9.37 g of 3-methylbenzonitrile were dissolved in 120 ml of chloroform, and 11.96 g of antimony pentachloride was added dropwise thereto at 0° C. The mixture was stirred at room temperature for 30 minutes and then refluxed for 16 hours. After cooling to room temperature, this was filtered under argon. The thus obtained antimony hexachloride salt of oxadiazinium was washed with dichloromethane and dried under a reduced pressure. When the oxadiazinium salt was gradually added to 400 ml of 28% aqueous ammonia at 0° C., white precipitate was formed. This was stirred at room temperature for 1 hour and filtered, and then the thus obtained white precipitate was washed with water and methanol. The white precipitate was dried and then dissolved by adding to boiling dimethylformamide, followed by filtration. The operation to add the insoluble component separated by filtration to boiling dimethylformamide and then to filtrate was further carried out three times. All of the filtrates were combined and cooled, and the white precipitate again formed was filtered and dried. It was confirmed by $^1$H- and $^{13}$C-NMR that the thus obtained white precipitate is 2-(4-bromophenyl)-4,6-di-m-tolyl-1,3,5-triazine (12.58 g, yield 76%).

$^1$H-NMR (CDCl$_3$): δ 2.56 (s, 6H), 7.42-7.55 (m, 4H), 7.74 (d, J=8.6 Hz, 2H), 8.54-8.62 (m, 4H), 8.68 (d, J=8.6 Hz, 2H).

$^{13}$C-NMR (CDCl$_3$): δ 21.5, 126.2, 127.3, 128.5, 129.4, 130.4, 131.8, 133.4, 135.2, 136.0, 138.3, 170.6, 171.7.

Reference Example 3

Synthesis of 2,4-bis(4-biphenylyl)-6-(4-bromophenyl)-1,3,5-triazine

A 4.39 g portion of 4-bromobenzoyl chloride and 7.17 g of 4-biphenylcarbonitrile were dissolved in 40 ml of chloroform, and 5.98 g of antimony pentachloride was added dropwise thereto at 0° C. The mixture was stirred at room temperature for 10 minutes and then refluxed for 13 hours. After cooling to room temperature, chloroform was evaporated under a reduced pressure. When the thus obtained 2,4-bis(4-biphenylyl)-6-(4-bromophenyl)-1,3,5-oxadiazinyl-1-ium hexachloroantimonate was gradually added to 300 ml of 28% aqueous ammonia at 0° C., white precipitate was formed. This was stirred at room temperature for 1 hour and filtered, and then the thus obtained white precipitate was washed with water and methanol. After drying the white precipitate, 150 ml of chloroform was added thereto, and this suspension was stirred under heating reflux and filtered. The operation to add 50 ml of chloroform to the insoluble component separated by filtration, to stir this under heating reflux and then to filtrate was further carried out twice. By combining all of the filtrates, evaporating chloroform under a reduced pressure and then recrystallizing the thus obtained solid from dichloromethane-methanol, a white solid of 2,4-bis(4-biphenylyl)-6-(4-bromophenyl)-1,3,5-triazine (9.48 g, yield 88%) was obtained.

$^1$H-NMR (CDCl$_3$): δ 7.30-7.39 (m, 2H), 7.39-7.49 (m, 4H), 7.59-7.68 (m, 4H), 7.65 (d, J=8.6 Hz, 2H), 7.74 (d, J=8.5 Hz, 4H), 8.59 (d, J=8.6 Hz, 2H), 8.76 (d, J=8.5 Hz, 4H).

$^{13}$C-NMR (CDCl$_3$): δ 127.2, 127.3, 127.4, 128.0, 128.9, 129.4, 130.4, 131.8, 134.9, 135.2, 140.3, 145.2, 170.7, 171.4.

Reference Example 4

Synthesis of 2-(4-bromophenyl)-4,6-bis(1-naphthyl)-1,3,5-triazine

A 1.10 g portion of 4-bromobenzoyl chloride and 1.53 g of naphthalene-1-carbonitrile were dissolved in 100 ml of chloroform, and 1.50 g of antimony pentachloride was added dropwise thereto at 0° C. The mixture was stirred at room temperature for 1 hour and then refluxed for 8 hours. After cooling to room temperature, chloroform was evaporated under a reduced pressure. When the thus obtained 2-(4-bromophenyl)-4,6-bis(1-naphthyl)-1,3,5-oxadiazinyl-1-ium hexachloroantimonate was gradually added to 100 ml of 28% aqueous ammonia at 0° C., white precipitate was formed. This was stirred at room temperature for 1 hour and filtered, and then the thus obtained white precipitate was washed with water and methanol. The white precipitate was dried, purified by a silica gel column chromatography (developing solvent hexane:chloroform=1:1) and then recrystallized from dichloromethane-methanol, thereby obtaining a white solid of 2-(4-bromophenyl)-4,6-bis(1-naphthyl)-1,3,5-triazine (0.91 g, yield 37%).

$^1$H-NMR (CDCl$_3$): δ 7.59 (ddd, J=8.0, 6.8, 1.2 Hz, 2H), 7.64 (ddd, J=8.5, 6.8, 1.5 Hz, 2H), 7.68 (dd, J=8.0, 7.4 Hz, 2H), 7.73 (d, J=8.6 Hz, 2H), 7.98 (brd, J=8.0 Hz, 2H), 8.10 (brd, J=8.0 Hz, 2H), 8.56 (dd, J=7.4, 1.2 Hz, 2H), 8.66 (d, J=8.6 Hz, 2H), 9.17 (brd, J=8.5 Hz, 2H).

$^{13}$C-NMR (CDCl$_3$): δ 125.2, 126.0, 126.2, 127.4, 127.8, 128.8, 130.6, 130.9, 131.3, 132.1, 132.5, 133.6, 134.2, 135.1, 170.4, 174.4.

Reference Example 5

Synthesis of 2-(4'-bromobiphenyl-4-yl)-4,6-bis(4-tert-butylphenyl)-1,3,5-triazine A 2.96 g portion of 4'-bromobiphenyl-4-carbonyl chloride and 3.18 g of 4-tert-butylbenzonitrile were dissolved in 30 ml of chloroform, and 2.99 g of antimony pentachloride was added dropwise thereto at 0° C. The mixture was stirred at room temperature for 10 minutes and then refluxed for 13 hours. After cooling to room temperature, chloroform was evaporated under a reduced pressure. When the thus obtained 2-(4'-bromobiphenyl-4-yl)-4,6-bis(4-tert-butylphenyl)-1,3,5-oxadiazinyl-1-ium hexachloroantimonate was gradually added to 150 ml of 28% aqueous ammonia at 0° C., white precipitate was formed. This was stirred at room temperature for 1 hour and filtered, and then the thus obtained white precipitate was washed with water and methanol. After drying the white precipitate, 150 ml of chloroform was added thereto, and this suspension was stirred under heating reflux and filtered. The operation to add 50 ml of chloroform to the insoluble component separated by filtration, to stir this under heating reflux and then to filtrate was further carried out twice. All of the filtrates were combined, chloroform was evaporated under a reduced pressure, and the thus obtained solid was recrystallized from dichloromethane-methanol. The thus obtained crude product was purified by a silica gel column chromatography (eluting solvent hexane:chloroform=9:1 to 4:1) and then recrystallized from dichloromethane-methanol, thereby obtaining a white solid of 2-(4'-bromobiphenyl-4-yl)-4,6-bis(4-tert-butylphenyl)-1,3,5-triazine (3.81 g, yield 66%).

$^1$H-NMR (CDCl$_3$): δ 1.42 (s, 18H), 7.57 (d, J=8.5 Hz, 2H), 7.61 (d, J=8.5 Hz, 4H), 7.62 (d, J=8.5 Hz, 2H), 7.75 (d, J=8.4 Hz, 2H), 8.70 (d, J=8.5 Hz, 4H), 8.82 (d, J=8.4 Hz, 2H).

$^{13}$C-NMR (CDCl$_3$): δ 31.2, 35.1, 122.3, 125.6, 127.0, 128.8, 128.8, 129.5, 132.0, 133.6, 135.8, 139.4, 143.6, 156.1, 171.0, 171.5.

Reference Example 6

Synthesis of 2-(4-biphenylyl)-4,6-bis(4-bromophenyl)-1,3,5-triazine

A 2.17 g portion of 4-biphenylcarbonyl chloride and 3.64 g of 4-bromobenzonitrile were dissolved in 60 ml of chloroform, and 2.99 g of antimony pentachloride was added dropwise thereto at 0° C. The mixture was stirred at room temperature for 10 minutes and then refluxed for 15 hours. After cooling to room temperature, chloroform was evaporated under a reduced pressure. When the thus obtained 2-(4-biphenylyl)-4,6-bis(4-bromophenyl)-1,3,5-oxadiazinyl-1-ium hexachloroantimonate was gradually added to 150 ml of 28% aqueous ammonia at 0° C., white precipitate was formed. This was stirred at room temperature for 1 hour and filtered, and then the thus obtained white precipitate was washed with water and methanol. After drying the white precipitate, 150 ml of chloroform was added thereto, and this suspension was stirred under heating reflux and filtered. The operation to add 50 ml of chloroform to the insoluble component separated by filtration, to stir this under heating reflux and then to filtrate was further carried out twice. All of the filtrates were combined, chloroform was evaporated under a reduced pressure, and the thus obtained solid was recrystallized from dichloromethane-methanol to obtain a white solid of 2-(4-biphenylyl)-4,6-bis(4-bromophenyl)-1,3,5-triazine (3.23 g, yield 59%).

$^1$H-NMR (CDCl$_3$): δ 7.40-7.45 (m, 1H), 7.48-7.53 (m, 2H), 7.69-7.75 (m, 2H), 7.72 (d, J=8.5 Hz, 4H), 7.81 (d, J=8.3 Hz, 2H), 8.64 (d, J=8.5 Hz, 4H), 8.80 (d, J=8.3 Hz, 2H).

Reference Example 7

Synthesis of 2,4-bis(4-biphenylyl)-6-(4'-bromobiphenyl-4-yl)-1,3,5-triazine

A 11.82 g portion of 4'-bromobiphenyl-4-carbonyl chloride and 14.34 g of 4-biphenylcarbonitrile were dissolved in 200 ml of chloroform, and 11.96 g of antimony pentachloride was added dropwise thereto at 0° C. The mixture was stirred at room temperature for 10 minutes and then refluxed for 12 hours. After cooling to room temperature, chloroform was evaporated under a reduced pressure. When the thus obtained 2,4-bis(4-biphenylyl)-6-(4'-bromobiphenyl-4-yl)-1,3,5-oxadiazinyl-1-ium hexachloroantimonate was gradually added to 600 ml of 28% aqueous ammonia at 0° C., white precipitate was formed. This was stirred at room temperature for 1 hour and filtered, and then the thus obtained white precipitate was washed with water and methanol. After drying the white precipitate, 300 ml of chloroform was added thereto, and this suspension was stirred under heating reflux and filtered. The operation to add 100 ml of chloroform to the insoluble component separated by filtration, to stir this under heating reflux and then to filtrate was further carried out twice. All of the filtrates were combined, chloroform was evaporated under a reduced pressure, and the thus obtained solid was recrystallized from dichloromethane-methanol to obtain a white solid of 2,4-bis(4-biphenylyl)-6-(4'-bromobiphenyl-4-yl)-1,3,5-triazine (19.88 g, yield 81%).

$^1$H-NMR (CDCl$_3$): δ 7.40-7.45 (m, 2H), 7.48-7.53 (m, 4H), 7.54 (d, J=8.5 Hz, 2H), 7.61 (d, J=8.5 Hz, 2H), 7.68-7.72 (m, 4H), 7.73 (d, J=8.4 Hz, 2H), 7.79 (d, J=8.4 Hz, 4H), 8.81 (d, J=8.4 Hz, 2H), 8.82 (d, J=8.4 Hz, 4H).

$^{13}$C-NMR (CDCl$_3$): δ 122.3, 127.0, 127.3, 128.0, 128.8, 128.9, 129.4, 129.5, 132.0, 135.1, 135.6, 139.3, 140.4, 143.7, 145.1, 171.1, 171.3.

Reference Example 8

Synthesis of 2,4-bis(4-biphenylyl)-6-[1,1':4',1"]terphenyl-4-yl-1,3,5-triazine

Under a stream of argon, 2.1 ml of a hexane solution containing 3.3 mmol of butyl lithium was slowly added to 30 ml of tetrahydrofuran cooled to −78° C. in which prepared by dissolving 0.69 g of 4-bromobiphenyl. After stirring at −78° C. for 15 minutes, 0.91 g of dichloro(tetramethylethylenediamine)zinc(II) was added thereto and stirred at −78° C. for 10 minutes and then at room temperature for 2.5 hours. A 1.35 g portion of 2,4-bis(4-biphenylyl)-6-(4-bromophenyl)-1,3,5-triazine prepared in Reference Example 3 and 0.12 g of tetrakis(triphenylphosphine)palladium(0) were dissolved in 60 ml of tetrahydrofuran and added to this solution, followed by stirring under heating reflux for 2 hours. The reaction solution was concentrated under a reduced pressure, and the thus obtained solid was purified by a silica gel column chromatography (developing solvent hexane:chloroform=2:1 to chloroform) and then recrystallized from dichloromethane-methanol to obtain a white solid of the intended 2,4-bis(4-biphenylyl)-6-[1,1':4',1"]terphenyl-4-yl-1,3,5-triazine (1.09 g, yield 71%).

$^1$H-NMR (CDCl$_3$): δ 7.37-7.45 (m, 3H), 7.46-7.54 (m, 6H), 7.68 (brd, J=8.4 Hz, 2H), 7.73 (brd, J=8.3 Hz, 4H), 7.74

(d, J=8.4 Hz, 2H), 7.81 (d, J=8.4 Hz, 2H), 7.83 (d, J=8.4 Hz, 4H), 7.87 (d, J=8.4 Hz, 2H), 8.88 (d, J=8.4 Hz, 4H), 8.89 (d, J=8.4 Hz, 2H).
$^{13}$C-NMR (CDCl$_3$): δ 127.1, 127.2, 127.3, 127.4, 127.5, 127.6, 127.7, 128.0, 128.9, 128.9, 129.5, 129.6, 135.2, 135.3, 139.3, 140.4, 140.6, 140.9, 144.6, 145.2, 171.4, 171.4.

Reference Example 9

Synthesis of 2,4-bis(1-naphthyl)-6-[1,1':4',1"]terphenyl-4-yl-1,3,5-triazine

Under a stream of argon, 2.8 ml of a hexane solution containing 4.3 mmol of butyl lithium was slowly added to 15 ml of tetrahydrofuran cooled to −78° C. in which prepared by dissolving 0.91 g of 4-bromobiphenyl. After stirring at −78° C. for 15 minutes, 1.19 g of dichloro(tetramethylethylenediamine)zinc(II) was added thereto and stirred at −78° C. for 10 minutes and then at room temperature for 2 hours. A 1.47 g portion of 2-(4-bromophenyl)-4,6-bis(1-naphthyl)-1,3,5-triazine prepared in Reference Example 4 and 0.14 g of tetrakis(triphenylphosphine)palladium(0) were dissolved in 80 ml of tetrahydrofuran and added to this solution, followed by stirring under heating reflux for 13 hours. The reaction solution was concentrated under a reduced pressure and the thus obtained solid was washed with chloroform to obtain a white solid of the intended 2,4-bis(1-naphthyl)-6-[1,1':4',1"]terphenyl-4-yl-1,3,5-triazine (1.19 g, yield 71%).
$^1$H-NMR (CDCl$_3$): δ 7.36-7.41 (m, 1H), 7.46-7.52 (m, 2H), 7.57-7.62 (m, 2H), 7.63-7.72 (m, 4H), 7.68 (dd, J=8.0, 7.3 Hz, 2H), 7.75 (d, J=8.4 Hz, 2H), 7.81 (d, J=8.4 Hz, 2H), 7.88 (d, J=8.5 Hz, 2H), 7.99 (brd, J=8.0 Hz, 2H), 8.10 (brd, J=8.0 Hz, 2H), 8.60 (dd, J=7.3 Hz, 1.2 Hz, 2H), 8.88 (d, J=8.5 Hz, 2H), 9.23 (brd, J=8.6 Hz, 2H).
$^{13}$C-NMR (CDCl$_3$): δ 125.2, 126.1, 127.1, 127.3, 127.4, 127.5, 127.6, 127.7, 128.7, 128.9, 129.7, 130.8, 131.4, 132.4, 133.9, 134.3, 135.1, 139.1, 140.1, 141.0, 144.9, 170.9, 174.3.

Example 1

Synthesis of 2,4-bis(4-tert-butylphenyl)-6-[4'-(2-pyridyl)biphenyl-4-yl]-1,3,5-triazine Under a stream of argon, 3.5 ml of a pentane solution containing 5.2 mmol of tert-butyl lithium was slowly added to 15 ml of tetrahydrofuran cooled to −78° C., and 10 ml of tetrahydrofuran in which 0.61 g of 2-(4-bromophenyl)pyridine was dissolved was further added dropwise to this solution. After stirring at −78° C. for 30 minutes, 1.64 g of dichloro(tetramethylethylenediamine)zinc(II) was added thereto and stirred at −78° C. for 10 minutes and then at room temperature for 2 hours. A 1.00 g portion of 2-(4-bromophenyl)-4,6-bis(4-tert-butylphenyl)-1,3,5-triazine prepared in Reference Example 1 and 0.12 g of tetrakis(triphenylphosphine)palladium(0) were dissolved in 35 ml of tetrahydrofuran and added to this solution, followed by stirring under heating reflux for 13 hours. The reaction solution was concentrated under a reduced pressure and the thus obtained solid was recrystallized from dichloromethane-methanol. The thus obtained crude product was purified by a silica gel column chromatography (eluting solution hexane:dichloromethane=3:2 to 4:3) and then again recrystallized from dichloromethane-methanol to obtain a white solid of the intended 2,4-bis(4-tert-butylphenyl)-6-[4'-(2-pyridyl)biphenyl-4-yl]-1,3,5-triazine (1.00 g, yield 87%). Its melting point and glass transition temperature are shown in Table 4.

$^1$H-NMR (CD$_2$Cl$_2$): δ 1.47 (s, 18H), 7.32 (ddd, J=6.8 Hz, 4.9 Hz, 1.8 Hz, 1H), 7.69 (d, J=8.7 Hz, 4H), 7.81-7.94 (m, 2H), 7.92 (d, J=8.6 Hz, 2H), 7.96 (d, J=8.6 Hz, 2H), 8.23 (d, J=8.6 Hz, 2H), 8.71-8.80 (m, 1H), 8.77 (d, J=8.6 Hz, 4H), 8.93 (d, J=8.5 Hz, 2H).
$^{13}$C-NMR (CD$_2$Cl$_2$): δ 31.4, 35.4, 120.6, 122.6, 126.0, 127.5, 127.6, 127.8, 129.1, 129.8, 134.0, 136.0, 137.1, 139.3, 141.0, 144.6, 150.1, 156.6, 156.8, 171.5, 171.8.

Example 2

Synthesis of 2-[4-(6-phenylpyridin-2-yl)phenyl]-4,6-di-m-tolyl-1,3,5-triazine

Under a stream of argon, 3.9 ml of a hexane solution containing 5.5 mmol of butyl lithium was slowly added to 100 ml of tetrahydrofuran cooled to −78° C. in which 2.08 g of 2-(4-bromophenyl)-4,6-di-m-tolyl-1,3,5-triazine synthesized by the method of Reference Example 2 had been dissolved. After stirring at −78° C. for 15 minutes, 1.16 g of trimethyltin chloride was added thereto and stirred at −78° C. for 30 minutes and then at room temperature for 30 minutes. After evaporating and drying tetrahydrofuran under a reduced pressure, 150 ml of toluene in which 1.36 g of 2-bromo-6-phenylpyridine had been dissolved and 0.58 g of tetrakis(triphenylphosphine)palladium(0) were added to the thus obtained solid and stirred under heating reflux for 17 hours. The reaction solution was concentrated under a reduced pressure and the thus obtained solid was recrystallized from dichloromethane-methanol. The thus obtained crude product was purified by a silica gel column chromatography (developing solvent hexane:dichloromethane=3:1 to 3:2) and then again recrystallized from dichloromethane-methanol to obtain a white solid of the intended 2-[4-(6-phenylpyridin-2-yl)phenyl]-4,6-di-m-tolyl-1,3,5-triazine (1.09 g, yield 44%). Its melting point and glass transition temperature are shown in Table 4.
$^1$H-NMR (CDCl$_3$): δ 2.58 (s, 6H), 7.43-7.61 (m, 7H), 7.77-7.96 (m, 3H), 8.19-8.27 (m, 2H), 8.42 (d, J=8.7 Hz, 2H), 8.59-8.67 (m, 4H), 8.95 (d, J=8.6 Hz, 2H).
$^{13}$C-NMR (CDCl$_3$): δ 21.6, 119.1, 119.3, 126.2, 127.1, 127.2, 128.6, 128.7, 129.2, 129.3, 129.5, 133.3, 136.3, 136.8, 137.7, 138.3, 139.2, 142.9, 155.9, 157.0, 171.3, 171.8.

Example 3

Synthesis of 2-[4-(5-phenylpyridin-2-yl)phenyl]-4,6-di-m-tolyl-1,3,5-triazine

Under a stream of argon, 3.0 ml of a hexane solution containing 4.2 mmol of butyl lithium was slowly added to 80 ml of tetrahydrofuran cooled to −78° C. in which g of 2-(4-bromophenyl)-4,6-di-m-tolyl-1,3,5-triazine obtained in Reference Example 2 had been dissolved. After stirring at −78° C. for 15 minutes, 0.87 g of trimethyltin chloride was added thereto and stirred at −78° C. for 45 minutes and then at room temperature for 30 minutes. After evaporating and drying tetrahydrofuran under a reduced pressure, 120 ml of toluene in which 1.07 g of 2-bromo-5-phenylpyridine had been dissolved and 0.44 g of tetrakis(triphenylphosphine)palladium(0) were added to the thus obtained solid and stirred under heating reflux for 3 days. The reaction solution was concentrated under a reduced pressure and the thus obtained solid was recrystallized from dichloromethane-methanol. The thus obtained crude product was purified by a silica gel column chromatography (eluting solution hexane:chloroform=3:2 to 1:1) and then again recrystallized from dichloromethane-methanol to obtain a white solid of the intended 2-[4-(5-phenylpyridin-2-yl)phenyl]-4,6-di-m-tolyl-1,3,5-triazine (0.14 g, yield 8%). Its melting point is shown in Table 4. Distinct point of glass transition was not observed.

$^1$H-NMR (CDCl$_3$): δ 2.48 (s, 6H), 7.33-7.51 (m, 7H), 7.56-7.64 (m, 2H), 7.84-7.99 (m, 2H), 8.21 (d, J=8.5 Hz, 2H), 8.49-8.58 (m, 4H), 8.84 (d, J=8.6 Hz, 2H), 8.95 (d, J=1.7 Hz, 1H).

$^{13}$C-NMR (CDCl$_3$): δ 21.6, 120.9, 126.3, 127.0, 127.1, 128.3, 128.6, 129.2, 129.5, 133.3, 135.3, 135.6, 136.2, 136.9, 137.4, 138.3, 142.4, 148.2, 155.2, 171.2, 171.8.

Example 4

Synthesis of 2-[4'-(2-pyridyl)biphenyl-4-yl]-4,6-di-m-tolyl-1,3,5-triazine

Under a stream of argon, 3.3 ml of a hexane solution containing 4.6 mmol of butyl lithium was slowly added to 100 ml of tetrahydrofuran cooled to −78° C. in which 1.75 g of 2-(4-bromophenyl)-4,6-di-m-tolyl-1,3,5-triazine obtained in Reference Example 2 had been dissolved. After stirring at −78° C. for 15 minutes, 0.96 g of trimethyltin chloride was added thereto and stirred at −78° C. for 1 hour and then at room temperature for 30 minutes. After evaporating and drying tetrahydrofuran under a reduced pressure, 150 ml of toluene in which 1.17 g of 2-(4-bromophenyl)pyridine had been dissolved and 0.49 g of tetrakis(triphenylphosphine)palladium(0) were added to the thus obtained solid and stirred under heating reflux for 24 hours. The reaction solution was concentrated under a reduced pressure and the thus obtained solid was recrystallized from dichloromethane-methanol. The thus obtained crude product was purified by a silica gel column chromatography (eluting solution hexane:dichloromethane=3:2 to 0:1) and then again recrystallized from dichloromethane-methanol to obtain a white solid of the intended 2-[4'-(2-pyridyl)biphenyl-4-yl]-4,6-di-m-tolyl-1,3,5-triazine (0.43 g, yield 21%). Its melting point and glass transition temperature are shown in Table 4.

$^1$H-NMR (CD$_2$Cl$_2$): δ 2.59 (s, 6H), 7.32 (ddd, J=6.7 Hz, 4.9 Hz, 1.8 Hz, 1H), 7.47-7.60 (m, 4H), 7.79-7.94 (m, 2H), 7.91 (d, J=8.6 Hz, 2H), 7.96 (d, J=8.5 Hz, 2H), 8.23 (d, J=8.6 Hz, 2H), 8.60-8.71 (m, 4H), 8.72-8.79 (m, 1H), 8.93 (d, J=8.5 Hz, 2H).

$^{13}$C-NMR (CD$_2$Cl$_2$): δ 21.7, 120.7, 122.7, 126.5, 127.6, 127.7, 127.8, 128.9, 129.7, 129.8, 133.7, 135.9, 136.6, 137.1, 139.0, 139.4, 141.0, 144.8, 150.1, 156.9, 171.6, 172.1.

Example 5

Synthesis of 2,4-bis(4-tert-butylphenyl)-6-[4-(5-phenylpyridin-2-yl)phenyl]-1,3,5-triazine Under a stream of argon, 3.5 ml of a pentane solution containing 5.2 mmol of tert-butyl lithium was slowly added to 15 ml of tetrahydrofuran cooled to −78° C., and 10 ml of tetrahydrofuran in which 0.61 g of 2-bromo-5-phenylpyridine had been dissolved was further added dropwise to this solution. After stirring at −78° C. for 30 minutes, 1.64 g of dichloro(tetramethylethylenediamine)zinc(II) was added thereto and stirred at −78° C. for 10 minutes and then at room temperature for 2 hours. A 35 ml portion of tetrahydrofuran prepared by dissolving 1.00 g of 2-(4-bromophenyl)-4,6-bis(4-tert-butylphenyl)-1,3,5-triazine synthesized by the method of Reference Example 1 and 0.12 g of tetrakis(triphenylphosphine)palladium(0) therein was added to this solution and stirred under heating reflux for 10 hours. The reaction solution was concentrated under a reduced pressure and the thus obtained solid was recrystallized from dichloromethane-methanol. The thus obtained crude product was purified by a silica gel column chromatography (eluting solution hexane:dichloromethane=3:2 to 4:3) and then again recrystallized from dichloromethane-methanol to obtain a white solid of the intended 2,4-bis(4-tert-butylphenyl)-6-[4-(5-phenylpyridin-2-yl)phenyl]-1,3,5-triazine (1.05 g, yield 91%). Its melting point is shown in Table 4. In this case, a distinct point of glass transition was not observed.

$^1$H-NMR (CDCl$_3$): δ 1.45 (s, 18H), 7.44-7.60 (m, 3H), 7.65 (d, J=8.6 Hz, 4H), 7.88 (d, J=8.5 Hz, 2H), 7.88-7.94 (m, 1H), 8.07-8.15 (m, 3H), 8.74 (d, J=8.6 Hz, 4H), 8.93 (d, J=8.5 Hz, 2H), 9.09 (d, J=1.7 Hz, 1H).

$^{13}$C-NMR (CDCl$_3$): δ 31.2, 35.1, 120.3, 125.6, 126.9, 127.0, 128.8, 129.1, 129.6, 133.6, 134.1, 135.1, 136.2, 138.8, 141.2, 148.1, 156.1, 156.6, 170.9, 171.5.

Example 6

Synthesis of 2-{4-[5-(4-tert-butylphenyl)pyridin-2-yl]phenyl}-4,6-di-m-tolyl-1,3,5-triazine Under a stream of argon, 5.3 ml of a pentane solution containing 7.8 mmol of tert-butyl lithium was slowly added to 25 ml of tetrahydrofuran cooled to −78° C., and 15 ml of tetrahydrofuran in which 1.13 g of 2-bromo-5-(4-tert-butylphenyl)pyridine had been dissolved was further added dropwise to this solution. After stirring at −78° C. for 30 minutes, 2.47 g of dichloro(tetramethylethylenediamine)zinc(II) was added thereto and stirred at −78° C. for 10 minutes and then at room temperature for 2 hours. A 50 ml portion of tetrahydrofuran prepared by dissolving 1.25 g of 2-(4-bromophenyl)-4,6-di-m-tolyl-1,3,5-triazine synthesized by the method of Reference Example 2 and 0.17 g of tetrakis(triphenylphosphine)palladium(0) therein was added to this solution and stirred under heating reflux for 3 hours. The reaction solution was concentrated under a reduced pressure and the thus obtained solid was recrystallized from dichloromethane-methanol. The thus obtained crude product was purified by a silica gel column chromatography (eluting solution hexane:dichloromethane=3:2 to 4:3) and then again recrystallized from dichloromethane-methanol to obtain a white solid of the intended 2-{4-[5-(4-tert-butylphenyl)pyridin-2-yl]phenyl}-4,6-di-m-tolyl-1,3,5-triazine (1.55 g, yield 94%). Its melting point is shown in Table 4. In this case, a distinct point of glass transition was not observed.

$^1$H-NMR (CDCl$_3$): δ 1.32 (s, 18H), 2.48 (s, 6H), 7.32-7.43 (m, 4H), 7.47 (d, J=8.7 Hz, 2H), 7.74-7.83 (m, 1H), 7.79 (d, J=8.6 Hz, 2H), 7.95 (d, J=8.6 Hz, 2H), 7.99 (dd, J=8.3 Hz, 2.4 Hz, 1H), 8.48-8.57 (m, 4H), 8.83 (d, J=8.6 Hz, 2H), (d, J=1.7 Hz, 1H).

$^{13}$C-NMR (CDCl$_3$): δ 21.6, 31.3, 34.7, 120.1, 125.8, 126.2, 126.6, 126.9, 128.5, 129.4, 129.7, 133.3, 133.7, 135.0, 135.9, 136.0, 136.2, 138.3, 141.4, 148.0, 152.4, 156.7, 171.0, 171.7.

Example 7

Synthesis of 6-{4-[4,6-bis(4-tert-butylphenyl)-1,3,5-triazin-2-yl]phenyl}-2,2'-bipyridyl Under a stream of argon, 1.4 ml of a hexane solution containing 2.2 mmol of butyl lithium was slowly added to 40 ml of tetrahydrofuran cooled to −78° C. in which 1.00 g of 2-(4-bromophenyl)-4,6-bis(4-tert-butylphenyl)-1,3,5-triazine obtained in Reference Example 1 had been dissolved. After stirring at −78° C. for 15 minutes, 0.61 g of dichloro (tetramethylethylenediamine)zinc(II) was added thereto and stirred at −78° C. for 10 minutes and then at room temperature for 2 hours. A 20 ml portion of tetrahydrofuran prepared by dissolving 0.56 g of 6-bromo-2,2'-bipyridyl and 0.12 g of tetrakis(triphenylphosphine)palladium(0) therein was added to this solution and stirred under heating reflux for 20 hours. The reaction solution was concentrated under a reduced pressure and the thus obtained solid was recrystallized from dichloromethane-methanol. The thus obtained crude product was purified by a silica gel column chromatography (developing solvent hexane:chloroform=1:1 to 0:1) and then again recrystallized from dichloromethane-methanol to obtain a white solid of the intended 6-{4-[4,6-bis(4-tert-butylphenyl)-1,3,5-triazin-2-yl]phenyl}-2,2'-bipyridyl (0.82 g, yield 71%). Its melting point and glass transition temperature are shown in Table 4.

$^1$H-NMR (CDCl$_3$): δ 1.45 (s, 18H), 7.39 (ddd, J=7.5 Hz, 4.7 Hz, 1.2 Hz, 1H), 7.65 (d, J=8.6 Hz, 4H), 7.88-8.03 (m, 3H), 8.40 (d, J=8.6 Hz, 2H), 8.48 (dd, J=7.2 Hz, 1.6 Hz, 1H), 8.69-8.78 (m, 2H), 8.75 (d, J=8.6 Hz, 4H), 8.94 (d, J=8.5 Hz, 2H).
$^{13}$C-NMR (CDCl$_3$): δ 31.2, 35.1, 119.9, 120.7, 121.4, 123.8, 125.6, 127.0, 128.8, 129.3, 133.7, 136.9, 136.9, 137.8, 142.8, 149.0, 155.6, 155.8, 156.0, 156.2, 171.0, 171.5.

Example 8

Synthesis of 5-{4-[4,6-bis(4-tert-butylphenyl)-1,3,5-triazin-2-yl]phenyl}-2,2'-bipyridyl Under a stream of argon, 0.35 ml of a hexane solution containing 0.55 mmol of butyl lithium was slowly added to 15 ml of tetrahydrofuran cooled to −78° C. in which 0.25 g of 2-(4-bromophenyl)-4,6-bis(4-tert-butylphenyl)-1,3,5-triazine obtained by Reference Example 1 had been dissolved. After stirring at −78° C. for 15 minutes, 0.15 g of dichloro(tetramethylethylenediamine)zinc(II) was added thereto and stirred at −78° C. for 10 minutes and then at room temperature for 2 hours. A 5 ml portion of tetrahydrofuran prepared by dissolving 0.14 g of 5-bromo-2,2'-bipyridyl and 0.03 g of tetrakis(triphenylphosphine)palladium(0) therein was added to this solution and stirred under heating reflux for 15 hours. The reaction solution was concentrated under a reduced pressure and the thus obtained solid was recrystallized from dichloromethane-methanol. The thus obtained crude product was purified by a silica gel column chromatography (eluting solution hexane:chloroform=1:1 to 0:1) and then again recrystallized from dichloromethane-methanol to obtain a white solid of the intended 5-{4-[4,6-bis(4-tert-butylphenyl)-1,3,5-triazin-2-yl]phenyl}-2,2'-bipyridyl (0.16 g, yield 56%). Its melting point and glass transition temperature are shown in Table 4.

$^1$H-NMR (CDCl$_3$): δ 1.45 (s, 18H), 7.38 (ddd, J=7.5 Hz, 4.8 Hz, 1.1 Hz, 1H), 7.65 (d, J=8.6 Hz, 4H), 7.84-7.95 (m, 1H), 7.90 (d, J=8.5 Hz, 2H), 8.14 (dd, J=8.3 Hz, 2.4 Hz, 1H), (d, J=8.0 Hz, 1H), 8.58 (d, J=8.2 Hz, 1H), 8.69-8.79 (m, 1H), 8.74 (d, J=8.6 Hz, 4H), 8.93 (d, J=8.5 Hz, 2H), 9.08 (d, J=1.8 Hz, 1H).
$^{13}$C-NMR (CDCl$_3$): δ 31.2, 35.1, 121.1, 121.2, 123.8, 125.6, 127.1, 128.8, 129.6, 133.6, 135.3, 135.7, 136.3, 137.0, 141.2, 147.7, 149.3, 155.4, 155.7, 156.1, 170.9, 171.6.

Example 9

Synthesis of 2,4-bis(4-tert-butylphenyl)-6-[4'-(5-phenylpyridin-2-yl)biphenyl-4-yl]-1,3,5-triazin Under a stream of argon, 0.35 ml of a hexane solution containing 0.55 mmol of butyl lithium was slowly added to 15 ml of tetrahydrofuran cooled to −78° C. in which 0.25 g of 2-(4-bromophenyl)-4,6-bis(4-tert-butylphenyl)-1,3,5-triazine obtained by Reference Example 1 had been dissolved. After stirring at −78° C. for 15 minutes, 0.15 g of dichloro(tetramethylethylenediamine)zinc(II) was added thereto and stirred at −78° C. for 10 minutes and then at room temperature for 2 hours. A 5 ml portion of tetrahydrofuran prepared by dissolving 0.19 g of 2-(4-bromophenyl)-5-phenylpyridine and 0.03 g of tetrakis(triphenylphosphine)palladium(0) therein was added to this solution and stirred under heating reflux for 14 hours. The reaction solution was concentrated under a reduced pressure and the thus obtained solid was recrystallized from dichloromethane-methanol. The thus obtained crude product was purified by a silica gel column chromatography (eluting solution hexane:chloroform=1:1 to 4:5) and then again recrystallized from dichloromethane-methanol to obtain a white solid of the intended 2,4-bis(4-tert-butylphenyl)-6-[4'-(5-phenylpyridin-2-yl)biphenyl-4-yl]-1,3,5-triazin (0.14 g, yield 43%). Its melting point is shown in Table 4. In this case, a distinct point of glass transition was not observed.

$^1$H-NMR (CDCl$_3$): δ 1.45 (s, 18H), 7.43-7.59 (m, 3H), 7.65 (d, J=8.6 Hz, 4H), 7.78-7.85 (m, 2H), 7.85-7.94 (m, 5H), 8.03-8.14 (m, 3H), 8.74 (d, J=8.6 Hz, 4H), 8.91 (d, J=8.5 Hz, 2H), 9.06 (d, J=1.7 Hz, 1H).
$^{13}$C-NMR (CDCl$_3$): δ 31.2, 35.1, 120.4, 125.6, 126.9, 127.2, 127.5, 128.0, 128.8, 129.1, 129.5, 133.7, 134.3, 135.0, 135.7, 137.2, 138.9, 140.1, 144.1, 148.0, 156.1, 156.3, 171.1, 171.6.

Example 10

Synthesis of 2,4-bis(4-tert-butylphenyl)-6-[4"-(2-pyridyl)-1,1':4',1"-terphenyl-4-yl]-1,3,5-triazine Under a stream of argon, 0.88 ml of a pentane solution containing 1.3 mmol of tert-butyl lithium was slowly added to 3 ml of tetrahydrofuran cooled to −78° C., and 7 ml of tetrahydrofuran in which 0.20 g of 4-bromo-4'-(2-pyridyl)-1,1'-biphenyl had been dissolved was added dropwise to this solution. After stirring at −78° C. for 30 minutes, 0.41 g of dichloro(tetramethylethylenediamine)zinc(II) was added thereto and stirred at −78° C. for 10 minutes and then at room temperature for 2 hours. A 10 ml portion of tetrahydrofuran prepared by dissolving 0.25 g of 2-(4-bromophenyl)-4,6-bis(4-tert-butylphenyl)-1,3,5-triazine obtained by Reference Example 1 and 0.03 g of tetrakis(triphenylphosphine)palladium(0) therein was added to this solution and stirred under heating reflux for 2 hours. The reaction solution was concentrated under a reduced pressure and the thus obtained solid was recrystallized from dichloromethane-methanol. The thus obtained crude product was purified by a silica gel column chromatography (eluting solution hexane:dichloromethane=1:1 to 0:1) and then again recrystallized from dichloromethane-methanol to obtain a white solid of the intended 2,4-bis(4-tert-butylphenyl)-6-[4"-(2-pyridyl)-1,1':4',1"-terphenyl-4-yl]-1,3,5-triazine (0.20 g, yield 61%). Its melting point is shown in Table 4. In this case, a distinct point of glass transition was not observed.

$^1$H-NMR (CD$_2$Cl$_2$): δ 1.34 (s, 18H), 7.18 (ddd, J=6.7 Hz, 4.9 Hz, 1.8 Hz, 1H), 7.56 (d, J=8.6 Hz, 4H), 7.67-7.79 (m, 8H), 7.83 (d, J=8.6 Hz, 2H), 8.08 (d, J=8.5 Hz, 2H), 8.59-8.64 (m, 1H), 8.64 (d, J=8.6 Hz, 4H), 8.80 (d, J=8.5 Hz, 2H).
$^{13}$C-NMR (CD$_2$Cl$_2$): δ 31.3, 35.4, 120.6, 122.6, 126.1, 127.5, 127.6, 127.8, 128.0, 129.1, 129.8, 134.0, 135.9, 137.1, 138.9, 139.7, 140.4, 141.2, 144.7, 150.1, 156.6, 157.0, 171.5, 171.9.

Example 11

Synthesis of 2,4-bis(4-biphenylyl)-6-[4'-(2-pyridyl)biphenyl-4-yl]-1,3,5-triazine Under a stream of argon, 4.1 ml of a pentane solution containing 6.0 mmol of tert-butyl lithium was slowly added to 15 ml of tetrahydrofuran cooled to −78° C., and 10 ml of tetrahydrofuran in which 0.70 g (3.0 mmol) of 2-(4-bromophenyl)pyridine had been dissolved was further added dropwise to this solution. After stirring at −78° C. for 30 minutes, 1.89 g (7.5 mmol) of dichloro(tetramethylethylenediamine)zinc(II) was added thereto and stirred at −78° C. for 10 minutes and then at room temperature for 2 hours. A 60 ml portion of tetrahydrofuran prepared by dissolving 1.35 g (2.5 mmol) of 2,4-bis-(4-biphenylyl)-6-(4-bromophenyl)-1,3,5-triazine obtained in Reference Example 3 and 0.12 g (0.10 mmol) of tetrakis(triphenylphosphine)palladium(0) therein was added to this solution and stirred under heating reflux for 13 hours. The reaction solution was concentrated under a reduced pressure and the thus obtained solid was recrystallized from dichloromethane-methanol. The thus obtained crude product was purified by a silica gel column chromatography (eluting solution hexane:dichloromethane=2:1 to 2:3) and an alumina gel column chromatography (eluting solution hexane:dichloromethane=2:1 to 1:2) and then again recrystallized from dichloromethane-methanol to obtain a white solid of the intended 2,4-bis(4-biphenylyl)-6-[4'-(2-pyridyl)biphenyl-4-yl]-1,3,5-triazine (1.19 g, yield 77%).

$^1$H-NMR (CD$_2$Cl$_2$): δ 7.28 (ddd, J=7.3, 4.8, 1.2 Hz, 1H), 7.40-7.46 (m, 2H), 7.48-7.54 (m, 4H), 7.72-7.77 (m, 4H), (ddd, J=7.6, 7.3, 1.8 Hz, 1H), 7.82-7.88 (m, 1H), (d, J=8.4 Hz, 4H), 7.86 (d, J=8.4 Hz, 2H), 7.91 (d, Hz, 2H), 8.18 (d, J=8.4 Hz, 2H), 8.72 (brd, J=4.8 Hz, 1H), 8.88 (d, J=8.4 Hz, 4H), 8.89 (d, J=8.4 Hz, 2H).

$^{13}$C-NMR (CD$_2$Cl$_2$): δ 120.7, 122.7, 127.6, 127.6, 127.7, 127.8, 127.8, 128.4, 129.3, 129.8, 129.9, 135.6, 135.8, 137.1, 139.4, 140.6, 141.0, 144.8, 145.5, 150.1, 156.9, 171.7, 171.7.

Example 12

Synthesis of 2,4-bis(1-naphthyl)-6-[4'-(2-pyridyl)biphenyl-4-yl]-1,3,5-triazine

Under a stream of argon, 4.1 ml of a pentane solution containing 6.0 mmol of tert-butyl lithium was slowly added to 15 ml of tetrahydrofuran cooled to −78° C., and 10 ml of tetrahydrofuran in which 0.70 g of 2-(4-bromophenyl)pyridine had been dissolved was further added dropwise to this solution. After stirring at −78° C. for 30 minutes, 1.89 g of dichloro(tetramethylethylenediamine)zinc(II) was added thereto and stirred at −78° C. for 10 minutes and then at room temperature for 2 hours. A 65 ml portion of tetrahydrofuran prepared by dissolving 1.22 g of 2-(4-bromophenyl)-4,6-bis(1-naphthyl)-1,3,5-triazine obtained in Reference Example 4 and 0.12 g of tetrakis(triphenylphosphine)palladium(0) therein was added to this solution and stirred under heating reflux for 16 hours. The reaction solution was concentrated under a reduced pressure and the thus obtained solid was recrystallized from dichloromethane-methanol. The thus obtained crude product was purified by a silica gel column chromatography (eluting solution hexane:dichloromethane=2:1 to chloroform) and an alumina gel column chromatography (eluting solution hexane:dichloromethane=2:1 to chloroform) and then again recrystallized from dichloromethane-methanol to obtain a white solid of the intended 2,4-bis(1-naphthyl)-6-[4'-(2-pyridyl)biphenyl-4-yl]-1,3,5-triazine (1.23 g, yield 87%).

$^1$H-NMR (CD$_2$Cl$_2$): δ 7.29-7.38 (m, 1H), 7.62 (ddd, J=8.0, 6.8, 1.3 Hz, 2H), 7.67 (ddd, J=8.6, 6.8, 1.5 Hz, 2H), 7.72 (dd, J=8.1, 7.3 Hz, 2H), 7.84-7.92 (m, 2H), 7.89 (d, J=8.3 Hz, 2H), 7.94 (d, J=8.5 Hz, 2H), 8.02 (brd, J=8.0 Hz, 2H), 8.14 (brd, J=8.1 Hz, 2H), 8.21 (d, J=8.3 Hz, 2H), 8.58 (dd, J=7.3, 1.2 Hz, 2H), 8.71-8.76 (m, 1H), 8.89 (d, J=8.5 Hz, 2H), 9.21 (brd, J=8.6 Hz, 2H).

$^{13}$C-NMR (CDCl$_3$): δ 120.5, 122.3, 125.2, 126.1, 127.3, 127.5, 127.6, 128.7, 129.7, 130.8, 131.4, 132.4, 133.9, 134.3, 135.2, 136.8, 139.0, 140.7, 144.8, 149.8, 156.8, 170.9, 174.3.

Example 13

Synthesis of 6-[4-(4,6-di-m-tolyl-1,3,5-triazin-2-yl)phenyl]-2,2'-bipyridyl

Under a stream of argon, 2.1 ml of a hexane solution containing 3.3 mmol of butyl lithium was slowly added to 60 ml of tetrahydrofuran cooled to −78° C. in which 1.25 g of 2-(4-bromophenyl)-4,6-di-m-tolyl-1,3,5-triazine obtained in Reference Example 2 had been dissolved. After stirring at −78° C. for 15 minutes, 0.91 g of dichloro(tetramethylethylenediamine)zinc(II) was added thereto and stirred at −78° C. for 10 minutes and then at room temperature for 2 hours. A 20 ml portion of tetrahydrofuran prepared by dissolving 0.85 g of 6-bromo-2,2'-bipyridyl and 0.14 g of tetrakis(triphenylphosphine)palladium(0) therein was added to this solution and stirred under heating reflux for 14 hours. The reaction solution was concentrated under a reduced pressure and the thus obtained solid was recrystallized from dichloromethane-methanol. The thus obtained crude product was purified by a silica gel column chromatography (developing solvent hexane:chloroform=1:1 to 1:2) and then again recrystallized from dichloromethane-methanol to obtain a white solid of the intended 6-[4-(4,6-di-m-tolyl-1,3,5-triazin-2-yl)phenyl]-2,2'-bipyridyl (0.89 g, yield 61%). Its melting point is shown in Table 4. In this case, a distinct point of glass transition was not observed.

$^1$H-NMR (CDCl$_3$): δ 2.54 (s, 6H), 7.36 (ddd, J=7.4, 4.8, 1.1 Hz, 1H), 7.41-7.45 (m, 2H), 7.48 (brdd, J=7.5, 7.5 Hz, 2H), 7.86-7.92 (m, 2H), 7.94 (dd, J=7.8, 6.7 Hz, 1H), 8.36 (d, J=8.5 Hz, 2H), 8.46 (brd, J=7.6 Hz, 1H), 8.57-8.62 (m, 4H), 8.69 (brd, J=7.8 Hz, 1H), 8.73 (brd, J=4.8 Hz, 1H), 8.90 (d, J=8.5 Hz, 2H).

$^{13}$C-NMR (CDCl$_3$): δ 21.7, 120.1, 120.9, 121.6, 124.0, 126.3, 127.1, 128.6, 129.4, 129.5, 133.4, 136.3, 136.9, 137.4, 137.9, 138.4, 142.9, 148.8, 155.5, 155.7, 156.0, 171.2, 171.8.

Example 14

Synthesis of 6-{4-[4,6-bis(4-biphenylyl)-1,3,5-triazin-2-yl]phenyl}-2,2'-bipyridyl Under a stream of argon, 2.1 ml of a hexane solution containing 3.3 mmol of butyl lithium was slowly added to 70 ml of tetrahydrofuran cooled to −78° C. in which 1.62 g of 2,4-bis(4-biphenylyl)-6-(4-bromophenyl)-1,3,5-triazine obtained in Reference Example 3 had been dissolved. After stirring at −78° C. for 15 minutes, 0.91 g of dichloro(tetramethylethylenediamine)zinc(II) was added thereto and stirred at −78° C. for 10 minutes and then at room temperature for 2 hours. A 20 ml portion of tetrahydrofuran prepared by dissolving 0.85 g of 6-bromo-2,2'-bipyridyl and 0.14 g of tetrakis(triphenylphosphine)palladium(0) therein was added to this solution and stirred under heating reflux for 4 hours. The reaction solution was concentrated under a reduced pressure and the thus obtained solid was recrystallized from dichloromethane-methanol. The thus obtained crude product was washed with chloroform to obtain a white solid of the intended 6-{4-[4,6-bis(4-biphenylyl)-1,3,5-triazin-2-yl]phenyl}-2,2'-bipyridyl (1.24 g, yield 67%).

$^1$H-NMR (CDCl$_3$): δ 7.36 (ddd, J=7.4, 4.8, 1.2 Hz, 1H), 7.41-7.45 (m, 2H), 7.50-7.54 (m, 4H), 7.72-7.76 (m, 4H), 7.84 (d, J=8.5 Hz, 4H), 7.90 (ddd, J=7.7, 7.4, 1.9 Hz, 1H), 7.93 (dd, J=7.8, 1.2 Hz, 1H), 7.97 (dd, J=7.8, 7.7 Hz, 1H), 8.40 (d, J=8.6 Hz, 2H), 8.46 (brdd, J=7.7, 1.2 Hz, 1H), 8.69-8.72 (m, 1H), 8.73 (ddd, J=4.8, 1.9, 0.9 Hz, 1H), 8.90 (d, J=8.5 Hz, 4H), 8.96 (d, J=8.6 Hz, 2H).

Example 15

Synthesis of 2,4-bis(4-tert-butylphenyl)-6-[4'-(3-pyridyl)biphenyl-4-yl]-1,3,5-triazine Under a stream of argon, 1.4 ml of a hexane solution containing 2.2 mmol of butyl lithium was slowly added to 50 ml of tetrahydrofuran cooled to −78° C. in which 1.15 g of 2-(4'-bromobiphenyl-4-yl)-4,6-bis(4-tert-butylphenyl)-1,3,5-triazine obtained in Reference Example 5 had been dissolved. After stirring at −78° C. for 15 minutes, 0.61 g of dichloro(tetramethylethylenediamine)zinc(II) was added thereto and stirred at −78° C. for 10 minutes and then at room temperature for 2 hours. A 10 ml portion of tetrahydrofuran prepared by dissolving 0.38 g of 3-bromopyridine and 0.09 g of tetrakis(triphenylphosphine)palladium(0) therein was added to this solution and stirred under heating reflux for 4 hours. The reaction solution was concentrated under a reduced pressure and the thus obtained solid was purified by a silica gel column chromatography (eluting solution hexane:chloroform=2:1 to chloroform) and an alumina gel column chromatography (eluting solution hexane:chloroform=2:1 to 3:2) and then recrystallized from dichloromethane-methanol to obtain a white solid of the intended 2,4-bis(4-tert-butylphenyl)-6-[4'-(3-pyridyl)biphenyl-4-yl]-1,3,5-triazine (0.71 g, yield 62%). Its melting point and glass transition temperature are shown in Table 4.

$^1$H-NMR (CDCl$_3$): δ 1.42 (s, 18H), 7.43 (brdd, J=7.8, 4.8 Hz, 1H), 7.61 (d, J=8.5 Hz, 4H), 7.72 (d, J=8.3 Hz, 2H), 7.83 (d, J=8.3 Hz, 2H), 7.84 (d, J=8.4 Hz, 2H), 7.95-8.00 (m, 1H), 8.64 (brdd, J=4.8, 1.5 Hz, 1H), 8.71 (d, J=8.5 Hz, 4H), 8.86 (d, J=8.4 Hz, 2H), 8.94 (brd, J=1.9 Hz, 1H).

$^{13}$C-NMR (CDCl$_3$): δ 31.2, 35.1, 123.8, 125.6, 127.2, 127.6, 128.0, 128.8, 129.5, 133.6, 134.7, 135.8, 136.3, 137.0, 140.3, 144.0, 147.7, 148.1, 156.0, 171.0, 171.5.

Example 16

Synthesis of 2,4-bis(4-biphenylyl)-6-[3'-(2-pyridyl)biphenyl-4-yl]-1,3,5-triazine Under a stream of argon, 4.1 ml of a pentane solution containing 6.0 mmol of tert-butyl lithium was slowly added to 20 ml of tetrahydrofuran cooled to −78° C., and 10 ml of tetrahydrofuran in which 0.70 g of 2-(3-bromophenyl)pyridine had been dissolved was further added dropwise to this solution. After stirring at −78° C. for 30 minutes, 1.89 g of dichloro(tetramethylethylenediamine)zinc(II) was added thereto and stirred at −78° C. for 10 minutes and then at room temperature for 2 hours. A 50 ml portion of tetrahydrofuran prepared by dissolving 1.35 g of 2,4-bis(4-biphenylyl)-6-(4-bromophenyl)-1,3,5-triazine obtained in Reference Example 3 and 0.12 g of tetrakis(triphenylphosphine)palladium(0) therein was added to this solution and stirred under heating reflux for 15 hours. The reaction solution was concentrated under a reduced pressure and the thus obtained solid was purified by a silica gel column chromatography (eluting solution hexane:chloroform=2:1 to chloroform) and an alumina gel column chromatography (eluting solution hexane:chloroform=2:1 to chloroform) and then recrystallized from dichloromethane-methanol and toluene to obtain a white solid of the intended 2,4-bis(4-biphenylyl)-6-[3'-(2-pyridyl)biphenyl-4-yl]-1,3,5-triazine (1.29 g, yield 84%).

$^1$H-NMR (CD$_2$Cl$_2$): δ 7.32 (ddd, J=7.2, 4.8, 1.2 Hz, 1H), 7.41-7.45 (m, 2H), 7.50-7.55 (m, 4H), 7.63 (brdd, J=7.7, 7.7 Hz, 1H), 7.74-7.78 (m, 4H), 7.80-7.90 (m, 3H), 7.87 (d, J=8.5 Hz, 4H), 7.96 (d, J=8.5 Hz, 2H), 8.07 (ddd, J=7.7, 1.3, 1.2 Hz, 1H), 8.42-8.44 (m, 1H), 8.74 (ddd, J=4.8, 1.7, 1.0 Hz, 1H), 8.90 (d, J=8.5 Hz, 4H), 8.92 (d, J=8.5 Hz, 2H).

$^{13}$C-NMR (CDCl$_3$): δ 120.8, 122.4, 126.0, 126.6, 127.4, 127.4, 127.6, 127.9, 128.1, 129.0, 129.4, 129.6, 135.3, 135.4, 136.9, 140.2, 140.5, 141.1, 145.1, 145.3, 149.9, 157.3, 171.5.

Example 17

Synthesis of 4-{4-[4,6-bis(4-biphenylyl)-1,3,5-triazin-2-yl]phenyl}-2,2'-bipyridyl Under a stream of argon, 20 ml of a toluene solution in which 0.54 g of 2,4-bis(4-biphenylyl)-6-(4-bromophenyl)-1,3,5-triazine obtained in Reference Example 3, 0.63 g of 4-tributylstannyl-2,2'-bipyridyl and 0.12 g of tetrakis(triphenylphosphine)palladium(0) had been dissolved was stirred under heating reflux for 15 hours. The reaction solution was concentrated under a reduced pressure and the thus obtained solid was purified by an alumina gel column chromatography (eluting solution hexane:chloroform=1:1 to chloroform) and then recrystallized from dichloromethane-methanol to obtain a white solid of the intended 4-{4-[4,6-bis(4-biphenylyl)-1,3,5-triazin-2-yl]phenyl}-2,2'-bipyridyl (0.48 g, yield 78%).

$^1$H-NMR (CDCl$_3$): δ 7.39-7.45 (m, 3H), 7.48-7.53 (m, 4H), 7.68 (dd, J=5.1, 1.7 Hz, 1H), 7.69-7.73 (m, 4H), 7.81 (d, J=8.5 Hz, 4H), 7.93 (ddd, J=7.8, 7.7, 1.5 Hz, 1H), 7.99 (d, J=8.4 Hz, 2H), 8.59 (brd, J=7.8 Hz, 1H), 8.78 (brd, J=4.8 Hz, 1H), 8.80 (brd, J=5.1 Hz, 1H), 8.84 (d, J=8.5 Hz, 4H), (brs, 1H), 8.90 (d, J=8.4 Hz, 2H).

$^{13}$C-NMR (CDCl$_3$): δ 119.3, 121.6, 121.8, 124.1, 127.3, 127.4, 127.5, 128.1, 129.0, 129.6, 129.7, 135.1, 137.1, 137.3, 140.4, 142.1, 145.3, 148.9, 149.2, 149.7, 155.8, 156.6, 171.1, 171.5.

Example 18

Synthesis of 2-(4-biphenylyl)-4,6-bis[4'-(2-pyridyl)biphenyl-4-yl]-1,3,5-triazine Under a stream of argon, 6.0 ml of a pentane solution containing 8.8 mmol of tert-butyl lithium was slowly added to 20 ml of tetrahydrofuran cooled to −78° C., and 10 ml of tetrahydrofuran in which 1.03 g of 2-(4-bromophenyl)pyridine had been dissolved was further added dropwise to this solution. After stirring at −78° C. for 30 minutes, 2.78 g of dichloro(tetramethylethylenediamine)zinc(II) was added thereto and stirred at −78° C. for 10 minutes and then at room temperature for 2 hours. A 60 ml portion of tetrahydrofuran prepared by dissolving 1.09 g of 2-(4-biphenylyl)-4,6-bis(4-bromophenyl)-1,3,5-triazine obtained in Reference Example 6 and 0.23 g of tetrakis(triphenylphosphine)palladium(0) therein was added to this solution and stirred under heating reflux for 16 hours. The reaction solution was concentrated under a reduced pressure and the thus obtained solid was purified by a silica gel column chromatography (eluting solution hexane:chloroform=2:1 to chloroform) and an alumina gel column chromatography (eluting solution hexane:chloroform=2:1 to chloroform) and then recrystallized from dichloromethane-methanol to obtain a white solid of the intended 2-(4-biphenylyl)-4,6-bis[4'-(2-pyridyl)biphenyl-4-yl]-1,3,5-triazine (1.06 g, yield 77%). Its melting point and glass transition temperature are shown in Table 4.

$^1$H-NMR (CD$_2$Cl$_2$): δ 7.33-7.40 (m, 2H), 7.41-7.46 (m, 1H), 7.50-7.55 (m, 2H), 7.74-7.79 (m, 2H), 7.88 (d, J=8.4 Hz, 2H), 7.88-7.93 (m, 8H), 7.95 (d, J=8.4 Hz, 4H), 8.23 (d, J=8.3 Hz, 4H), 8.75 (brd, J=4.7 Hz, 2H), 8.91 (d, J=8.4 Hz, 2H), 8.93 (d, J=8.4 Hz, 4H).

$^{13}$C-NMR (CDCl$_3$): δ 120.6, 122.3, 127.4, 127.4, 127.5, 127.7, 128.1, 129.0, 129.6, 129.6, 129.6, 135.3, 135.5, 136.9, 139.0, 140.5, 140.9, 144.6, 145.3, 149.9, 156.9, 171.4, 171.5.

Example 19

Synthesis of 5-{4-[4,6-bis(4-tert-butylphenyl)-1,3,5-triazin-2-yl]phenyl}-2,4'-bipyridyl Under a stream of argon, 2.1 ml of a hexane solution containing 3.2 mmol of butyl lithium was slowly added to 50 ml of tetrahydrofuran cooled to −78° C. in which 1.50 g of 2-(4-bromophenyl)-4,6-bis(4-tert-butylphenyl)-1,3,5-triazine obtained in Reference Example 1 had been dissolved. After stirring at −78° C. for 15 minutes, 0.83 g of dichloro(tetramethylethylenediamine)zinc(II) was added thereto and stirred at −78° C. for 10 minutes and then at room temperature for 2 hours. A 30 ml portion of tetrahydrofuran prepared by dissolving 0.74 g of 5-bromo-2,4'-bipyridyl and 0.14 g of tetrakis(triphenylphosphine)palladium(0) therein was added to this solution and stirred under heating reflux for 13 hours. The reaction solution was concentrated under a reduced pressure and the thus obtained solid was purified by a silica gel column chromatography (eluting solution hexane:chloroform=2:1 to chloroform) and an alumina gel column chromatography (eluting solution hexane:chloroform=1:1) and then recrystallized from dichloromethane-methanol to obtain a white solid of the intended 5-{4-[4,6-bis(4-tert-butylphenyl)-1,3,5-triazin-2-yl]phenyl}-2,4'-bipyridyl (0.97 g, yield 56%). Its melting point is shown in Table 4. In this case, a distinct point of glass transition was not observed.

$^1$H-NMR (CDCl$_3$): δ 1.42 (s, 18H), 7.61 (d, J=8.5 Hz, 4H), 7.83 (d, J=8.4 Hz, 2H), 7.92 (brd, J=8.2 Hz, 1H), 8.00 (d, J=6.1 Hz, 2H), 8.10 (dd, J=8.2, 2.4 Hz, 1H), 8.70 (d, J=8.5 Hz, 4H), 8.76 (d, J=6.1 Hz, 2H), 8.88 (d, J=8.4 Hz, 2H), 9.08 (brd, J=2.4 Hz, 1H).

$^{13}$C-NMR (CDCl$_3$): δ 31.3, 35.2, 120.9, 121.2, 125.7, 127.3, 128.9, 129.8, 133.6, 135.5, 136.2, 136.7, 140.7, 146.5, 148.7, 149.9, 153.5, 156.3, 170.8, 171.7.

Example 20

Synthesis of 5-{4-[4,6-bis(4-biphenylyl)-1,3,5-triazin-2-yl]phenyl}-2,4'-bipyridyl Under a stream of argon, 2.2 ml of a hexane solution containing 3.3 mmol of butyl lithium was slowly added to 60 ml of tetrahydrofuran cooled to −78° C. in which 1.62 g of 2,4-bis(4-biphenylyl)-6-(4-bromophenyl)-1,3,5-triazine obtained in Reference Example 3 had been dissolved. After stirring at −78° C. for 15 minutes, 0.91 g of dichloro(tetramethylethylenediamine)zinc(II) was added thereto and stirred at −78° C. for 10 minutes and then at room temperature for 2 hours. A 30 ml portion of tetrahydrofuran prepared by dissolving 0.71 g of 5-bromo-2,4'-bipyridyl and 0.14 g of tetrakis(triphenylphosphine)palladium(0) therein was added to this solution and stirred under heating reflux for 14 hours. The reaction solution was concentrated under a reduced pressure and the thus obtained solid was recrystallized from dichloromethane-methanol. The thus obtained crude product was purified by a silica gel column chromatography (eluting solution hexane:chloroform=2:1 to chloroform) and an alumina gel column chromatography (eluting solution hexane:chloroform=1:1) and then recrystallized from dichloromethane-methanol to obtain a white solid of the intended 5-{4-[4,6-bis(4-biphenylyl)-1,3,5-triazin-2-yl]phenyl}-2,4'-bipyridyl (1.00 g, yield 54%).

$^1$H-NMR (CDCl$_3$): δ 7.40-7.45 (m, 2H), 7.48-7.54 (m, 4H), 7.69-7.75 (m, 4H), 7.82 (d, J=8.4 Hz, 4H), 7.86 (d, J=8.4 Hz, 2H), 7.93 (brd, J=8.2 Hz, 1H), 7.98 (d, J=6.1 Hz, 2H), 8.12 (dd, J=8.2, 2.4 Hz, 1H), 8.77 (d, J=6.1 Hz, 2H), 8.86 (d, J=8.4 Hz, 4H), 8.92 (d, J=8.4 Hz, 2H), 9.10 (brd, J=2.4 Hz, 1H).

$^{13}$C-NMR (CDCl$_3$): δ 120.9, 121.1, 127.3, 127.3, 127.4, 128.1, 129.0, 129.6, 129.9, 135.1, 135.5, 136.0, 136.5, 140.4, 140.9, 145.4, 146.1, 148.7, 150.4, 153.8, 171.1, 171.5.

Example 21

Synthesis of 2,4-bis(4-biphenylyl)-6-[4'-(3-pyridyl)biphenyl-4-yl]-1,3,5-triazine Under a stream of argon, 5.7 ml of an aqueous solution in which 1.44 g of tripotassium phosphate was dissolved was added to 70 ml of a 1,4-dioxane solution prepared by dissolving 2.47 g of 2,4-bis(4-biphenylyl)-6-(4'-bromobiphenyl-4-yl)-1,3,5-triazine obtained in Reference Example 7, 0.54 g of 3-pyridine borate, 0.04 g of tris(dibenzylideneacetone)dipalladium(0) and 0.03 g of tricyclohexylphosphine therein and stirred under heating reflux for 13 hours. The reaction solution was concentrated under a reduced pressure, the thus obtained solid was dissolved in chloroform, and the organic layer was washed with water and then dried using magnesium sulfate. Magnesium sulfate was separated by filtration, chloroform was evaporated under a reduced pressure, and the thus obtained solid was purified by a silica gel column chromatography (eluting solution hexane:chloroform=2:1 to 1:2) and then recrystallized from dichloromethane-methanol to obtain a white solid of the intended 2,4-bis(4-biphenylyl)-6-[4'-(3-pyridyl)biphenyl-4-yl]-1,3,5-triazine (2.24 g, yield 91%). Its melting point and glass transition temperature are shown in Table 4.

$^1$H-NMR (CDCl$_3$): δ 7.38-7.45 (m, 3H), 7.48-7.54 (m, 4H), 7.69-7.75 (m, 6H), 7.79-7.85 (m, 2H), 7.81 (d, J=8.3 Hz, 4H), 7.85 (d, J=8.4 Hz, 2H), 7.92-7.96 (m, 1H), 8.64 (brdd, J=4.8, 1.5 Hz, 1H), 8.86 (d, J=8.3 Hz, 4H), 8.87 (d, J=8.4 Hz, 2H), 8.94 (brd, J=2.0 Hz, 1H).

$^{13}$C-NMR (CDCl$_3$): δ 123.7, 127.3, 127.3, 127.4, 127.7, 128.0, 128.1, 129.0, 129.6, 129.6, 134.3, 135.2, 135.6, 136.1, 137.5, 140.2, 140.5, 144.3, 145.2, 148.3, 148.8, 171.3, 171.4.

Example 22

Synthesis of 2,4-bis(4-biphenylyl)-6-[4'-(4-pyridyl)biphenyl-4-yl]-1,3,5-triazine Under a stream of argon, 5.7 ml of an aqueous solution in which 1.44 g of tripotassium phosphate was dissolved was added to 70 ml of a 1,4-dioxane solution prepared by dissolving 2.47 g of 2,4-bis(4-biphenylyl)-6-(4'-bromobiphenyl-4- yl)-1,3,5-triazine obtained in Reference Example 7, 0.54 g of 4-pyridine borate, 0.04 g of tris(dibenzylideneacetone)dipalladium(0) and 0.03 g of tricyclohexylphosphine therein and stirred under heating reflux for 14 hours. The reaction solution was concentrated under a reduced pressure, the thus obtained solid was dissolved in chloroform, and the organic layer was washed with water and then dried using magnesium sulfate. Magnesium sulfate was separated by filtration, chloroform was evaporated under a reduced pressure, and the thus obtained solid was purified by a silica gel column chromatography (eluting solution hexane:chloroform=2:1 to chloroform) and then recrystallized from dichloromethane-methanol to obtain a white solid of the intended 2,4-bis(4-biphenylyl)-6-[4'-(4-pyridyl)biphenyl-4-yl]-1,3,5-triazine (2.35 g, yield 96%). Its melting point and glass transition temperature are shown in Table 4.

$^1$H-NMR (CDCl$_3$): δ 7.41-7.45 (m, 2H), 7.48-7.54 (m, 4H), 7.68 (d, J=6.2 Hz, 2H), 7.70-7.74 (m, 4H), 7.78-7.87 (m, 6H), 7.82 (d, J=8.4 Hz, 4H), 8.72 (d, J=6.2 Hz, 2H), 8.86 (d, J=8.4 Hz, 4H), 8.88 (d, J=8.5 Hz, 2H).

$^{13}$C-NMR (CDCl$_3$): δ 122.0, 127.3, 127.4, 127.7, 128.1, 128.2, 129.0, 129.6, 129.7, 135.2, 135.9, 136.8, 140.4, 141.8, 143.9, 145.3, 148.5, 149.6, 171.2, 171.5.

Example 23

Preparation and Performance Evaluation of an Organic Electroluminescence Device which Comprises 2,4-bis(4-tert-butylphenyl)-6-[4'-(2-pyridyl) biphenyl-4-yl]-1,3,5-triazine as a Composing Component A glass substrate equipped with an ITO transparent electrode, on which an indium-tin oxide (ITO) film of 2 mm in width was patterned in stripes, was used as the substrate. This substrate was washed with isopropyl alcohol and then subjected to a surface treatment by ultraviolet ray-ozone washing. An organic electroluminescence device of 4 mm$^2$ in luminescent area having a sectional view as shown in FIG. 1 was prepared by carrying out a vacuum evaporation of each layer on the substrate after washing by a vacuum evaporation method.

Firstly, the aforementioned glass substrate was put into a vacuum evaporation vessel, followed by decompression to 1.0×10$^{-4}$ Pa. Thereafter, films of a hole injection layer 2, a hole transporting layer 3, an emissive layer 4 and an electron transporting layer 5 were formed in that order as the organic compound layers on the aforementioned glass substrate shown by FIG. 1(1), and then a film of a cathode layer 6 was formed. As the hole injection layer 2, copper(II) phthalocyanine purified by sublimation was vacuum-evaporated with a film thickness of 25 nm. As the hole transporting layer 3, N,N'-di(naphthylen-1-yl)-N,N'-diphenylbenzidine (NPD) was vacuum-evaporated with a film thickness of 45 nm. As the emissive layer 4, Alq was vacuum-evaporated with a film thickness of 40 nm. As the electron transporting layer 5, 2,4-bis(4-tert-butylphenyl)-6-[4'-(2-pyridyl)biphenyl-4-yl]-1,3,5-triazine obtained in Example 1 was vacuum-evaporated with a film thickness of 20 nm. Additionally, film-formation of each organic material was performed by a resistance heating system, and the heated compound was vacuum-evaporated at a film formation rate of from 0.3 to 0.5 nm/second. Finally, a film of the cathode layer 6 was formed by arranging a metal mask orthogonally to the ITO stripe. The cathode layer 6 was made into a double layer structure by vacuum-evaporating lithium fluoride and aluminum to respective film thicknesses of 0.5 nm and 100 nm, respectively. Each film thickness was measured by a contact type surface profiliometer (DEKTAK). In addition, this device was sealed using a glove box under a nitrogen atmosphere of 1 ppm or less in oxygen and moisture concentrations. A sealing cap made of glass and the aforementioned film forming substrate epoxy-type ultraviolet cure adhesive (mfd. by Nagase Chemtex) were used in the sealing.

By applying a direct current to the thus prepared organic electroluminescence device, its luminescence characteristics were evaluated using a luminance meter LUMINANCE METER (BM-9) manufactured by TOPCON. As the luminescence characteristics, luminance (cd/m$^2$), luminous efficiency (cd/m$^2$) and emission wavelength (nm) at a voltage of 6.0 V were measured. Also, the device lifetime was defined as a luminance half-decay time (h) of initial luminance by constant current drive, wherein the initial luminance is a value when an electric current of 1 mA was applied. The results are shown in Table 5. In addition, driving voltage (V), luminance (cd/m$^2$), electric power efficiency (lm/W) and emission wavelength (nm) were measured when an electric current of 1 mA in voltage was applied were measured. The results are shown in Table 6.

Example 24

Preparation and Performance Evaluation of an Organic Electroluminescence Device which Comprises 2,4-bis(4-tert-butylphenyl)-6-[4-(5-phenylpyridin-2-yl)phenyl]-1,3,5-triazine as a Composing Component An organic electroluminescence device in which the 2,4-bis(4-tert-butylphenyl)-6-[4-(5-phenylpyridin-2-yl)phenyl]-1,3,5-triazine obtained in Example 5 was used as the electron transporting layer 5, instead of the 2,4-bis(4-tert-butylphenyl)-6-[4'-(2-pyridyl)biphenyl-4-yl]-1,3,5-triazin in Example 23, and vacuum-evaporated with a film thickness of 20 nm was prepared in the same manner as in Example 23.

Evaluation of the thus prepared organic electroluminescence device was also carried out in the same manner as in Example 23. The results are shown in Table 5 and Table 6.

Example 25

Preparation and Performance Evaluation of an Organic Electroluminescence Device which Comprises 2-{4-[5-(4-tert-butylphenyl)pyridin-2-yl]phenyl}-4,6-di-m-tolyl-1,3,5-triazine as a Composing Component An organic electroluminescence device in which the 2-{4-[5-(4-tert-butylphenyl)pyridin-2-yl]phenyl}4,6-di-m-tolyl-1,3,5-triazine obtained in Example 6 was used as the electron transporting layer 5, instead of the 2,4-bis(4-tert-butylphenyl)-6-[4'-(2-pyridyl)biphenyl-4-yl]-1,3,5-triazin in Example 23, and vacuum-evaporated with a film thickness of 20 nm was prepared in the same manner as in Example 23.

Evaluation of the thus prepared organic electroluminescence device was also carried out in the same manner as in Example 23. The results are shown in Table 5 and Table 6.

Comparative Example 1

An organic electroluminescence device in which a general purpose electron transporting material Alq was used as the electron transporting layer 5, instead of the 2,4-bis(4-tert-butylphenyl)-6-[4'-(2-pyridyl)biphenyl-4-yl]-1,3,5-triazin in Example 23, and vacuum-evaporated with a film thickness of 20 nm was prepared in the same manner as in Example 23.

Evaluation of the thus prepared organic electroluminescence device was also carried out in the same manner as in Example 23. The results are shown in Table 5.

Example 26

Preparation and Performance Evaluation of an Organic Electroluminescence Device which Comprises 2,4-bis(4-biphenylyl)-6-[4'-(2-pyridyl)biphenyl-4-yl]-1,3,5-triazine as a Composing Component An organic electroluminescence device in which the 2,4-bis(4-biphenylyl)-6-[4'-(2-pyridyl)biphenyl-4-yl]-1,3,5-triazine obtained in Example 11 was used as the electron transporting layer 5, instead of the 2,4-bis(4-tert-butylphenyl)-6-[4'-(2-pyridyl)biphenyl-4-yl]-1,3,5-triazin in Example 23, and vacuum-evaporated with a film thickness of 20 nm was prepared in the same manner as in Example 23.

Evaluation of the thus prepared organic electroluminescence device was also carried out in the same manner as in Example 23. The results are shown in Table 5 and Table 6.

Example 27

Preparation and Performance Evaluation of an Organic Electroluminescence Device which Comprises 2,4-bis(1-naphthyl)-6-[4'-(2-pyridyl)biphenyl-4-yl]-1,3,5-triazine as a Composing Component An organic electroluminescence device in which the 2,4-bis(1-naphthyl)-6-[4'-(2-pyridyl)biphenyl-4-yl]-1,3,5-triazine obtained in Example 12 was used as the electron transporting layer 5, instead of the 2,4-bis(4-tert-butylphenyl)-6-[4'-(2-pyridyl)biphenyl-4-yl]-1,3,5-triazin in Example 23, and vacuum-evaporated with a film thickness of 20 nm was prepared in the same manner as in Example 23.

Evaluation of the thus prepared organic electroluminescence device was also carried out in the same manner as in Example 23. The results are shown in Table 5 and Table 6.

Example 28

Preparation and Performance Evaluation of an Organic Electroluminescence Device which Comprises 5-{4-[4,6-bis(4-tert-butylphenyl)-1,3,5-triazin-2-yl]phenyl}2,2'-bipyridyl as a Composing Component An organic electroluminescence device in which the 5-{4-[4,6-bis(4-tert-butylphenyl)-1,3,5-triazin-2-yl]phenyl}2,2'-bipyridyl obtained in Example 8 was used as the electron transporting layer 5, instead of the 2,4-bis(4-tert-butylphenyl)-6-[4'-(2-pyridyl)biphenyl-4-yl]-1,3,5-triazin in Example 23, and vacuum-evaporated with a film thickness of 20 nm was prepared in the same manner as in Example 23.

Evaluation of the thus prepared organic electroluminescence device was also carried out in the same manner as in Example 23. The results are shown in Table 5 and Table 6.

Example 29

Preparation and Performance Evaluation of an Organic Electroluminescence Device which Comprises 6-[4-(4,6-di-m-tolyl-1,3,5-triazin-2-yl)phenyl]2,2'-bipyridyl as a Composing Component An organic electroluminescence device in which the 6-[4-(4,6-di-m-tolyl-1,3,5-triazin-2-yl)phenyl]2,2'-bipyridyl obtained in Example 13 was used as the electron transporting layer 5, instead of the 2,4-bis(4-tert-butylphenyl)-6-[4'-(2-pyridyl)biphenyl-4-yl]-1,3,5-triazin in Example 23, and vacuum-evaporated with a film thickness of 20 nm was prepared in the same manner as in Example 23.

Evaluation of the thus prepared organic electroluminescence device was also carried out in the same manner as in Example 23. The results are shown in Table 5 and Table 6.

Example 30

Preparation and Performance Evaluation of an Organic Electroluminescence Device which Comprises 2-(4-biphenylyl)-4,6-bis[4'-(2-pyridyl)biphenyl-4-yl]-1,3,5-triazine as a Composing Component An organic electroluminescence device in which the 2-(4-biphenylyl)-4,6-bis[4'-(2-pyridyl)biphenyl-4-yl]-1,3,5-triazine obtained in Example 18 was used as the electron transporting layer 5, instead of the 2,4-bis(4-tert-butylphenyl)-6-[4'-(2-pyridyl)biphenyl-4-yl]-1,3,5-triazin in Example 23, and vacuum-evaporated with a film thickness of 20 nm was prepared in the same manner as in Example 23.

Evaluation of the thus prepared organic electroluminescence device was also carried out in the same manner as in Example 23. The results are shown in Table 5 and Table 6.

Example 31

Preparation and Performance Evaluation of an Organic Electroluminescence Device which Comprises 2,4-bis(4-biphenylyl)-6-[4'-(3-pyridyl)biphenyl-4-yl]-1,3,5-triazine as a Composing Component An organic electroluminescence device in which the 2,4-bis(4-biphenylyl)-6-[4'-(3-pyridyl)biphenyl-4-yl]-1,3,5-triazine obtained in Example 21 was used as the electron transporting layer 5, instead of the 2,4-bis(4-tert-butylphenyl)-6-[4'-(2-pyridyl)biphenyl-4-yl]-1,3,5-triazin in Example 23, and vacuum-evaporated with a film thickness of 20 nm was prepared in the same manner as in Example 23.

Evaluation of the thus prepared organic electroluminescence device was also carried out in the same manner as in Example 23. The results are shown in Table 5 and Table 6.

Example 32

Preparation and Performance Evaluation of an Organic Electroluminescence Device which Comprises 2,4-bis(4-biphenylyl)-6-[4'-(4-pyridyl)biphenyl-4-yl]-1,3,5-triazine as a Composing Component An organic electroluminescence device in which the 2,4-bis(4-biphenylyl)-6-[4'-(4-pyridyl)biphenyl-4-yl]-1,3,5-triazine obtained in Example 22 was used as the electron transporting layer 5, instead of the 2,4-bis(4-tert-butylphenyl)-6-[4'-(2-pyridyl)biphenyl-4-yl]-1,3,5-triazin in Example 23, and vacuum-evaporated with a film thickness of 20 nm was prepared in the same manner as in Example 23.

Evaluation of the thus prepared organic electroluminescence device was also carried out in the same manner as in Example 23. The results are shown in Table 5 and Table 6.

Comparative Example 2

Using the same device of Comparative Example 1, its evaluation was carried out in the same manner as in Example 23. The results are shown in Table 6.

Comparative Example 3

Preparation and Performance Evaluation of an Organic Electroluminescence Device which Comprises 2,4-bis(4-biphenylyl)-6-[1,1':4',1"]terphenyl-4-yl-1,3,5-triazine as a Composing Component An organic electroluminescence device in which the 2,4-bis(4-biphenylyl)-6-[1,1':4',1"]terphenyl-4-yl-1,3,5-triazine obtained in Reference Example 8 was used as the electron transporting layer 5, instead of the 2,4-bis(4-tert-butylphenyl)-6-[4'-(2-pyridyl)biphenyl-4-yl]-1,3,5-triazin in Example 23, and vacuum-evaporated with a film thickness of 20 nm was prepared in the same manner as in Example 23.

Evaluation of the thus prepared organic electroluminescence device was carried out in the same manner as in Example 23. The results are shown in Table 6.

Comparative Example 4

Preparation and Performance Evaluation of an Organic Electroluminescence Device which Comprises 2,4-bis(1-naphthyl)-6-[1,1':4',1"]terphenyl-4-yl-1,3,5-triazine as a Composing Component An organic electroluminescence device in which the 2,4-bis(1-naphthyl)-6-[1,1':4',1"]terphenyl-4-yl-1,3,5-triazine obtained in Reference Example 9 was used as the electron transporting layer 5, instead of the 2,4-bis(4-tert-butylphenyl)-6-[4'-(2-pyridyl)biphenyl-4-yl]-1,3,5-triazin in Example 23, and vacuum-evaporated with a film thickness of 20 nm was prepared in the same manner as in Example 23.

Evaluation of the thus prepared organic electroluminescence device was carried out in the same manner as in Example 23. The results are shown in Table 6.

TABLE 4

|  | Melting point/° C. | Glass transition temperature/° C. |
|---|---|---|
| Example 1 | 225 | 173 |
| Example 2 | 198 | 193 |
| Example 3 | 235 | — |
| Example 4 | 231 | 222 |
| Example 5 | 254 | — |
| Example 6 | 239 | — |
| Example 7 | 235 | 227 |
| Example 8 | 271 | 137 |
| Example 9 | 303 | — |
| Example 10 | 290 | — |
| Example 13 | 214 | — |
| Example 15 | 224 | 117 |
| Example 18 | 340 | 177 |
| Example 19 | 278 | — |
| Example 21 | 261 | 188 |
| Example 22 | 288 | 177 | a) —: Distinct glass transition temperature was not observed.

TABLE 5

|  | Luminance (cd/m$^2$) | Luminous efficiency (cd/A) | Emission wavelength (nm) | Device lifetime (h) |
|---|---|---|---|---|
| Example 23 | 1224 | 3.97 | 517 | 1120 |
| Example 24 | 1106 | 4.71 | 517 | 1350 |
| Example 25 | 857 | 4.49 | 518 | 1070 |
| Example 26 | 1320 | 4.82 | 516 | 1250 |
| Example 27 | 1392 | 4.99 | 516 | 1150 |
| Example 28 | 1285 | 4.52 | 517 | 1095 |
| Example 29 | 1200 | 5.59 | 518 | 1105 |
| Example 30 | 3180 | 4.38 | 516 | 1720 |
| Example 31 | 1527 | 4.58 | 518 | 1070 |
| Example 32 | 1034 | 4.64 | 518 | 1020 |
| Comp. Ex. 1 | 1013 | 3.79 | 516 | 1050 |

TABLE 6

|  | Driving voltage (V) | Luminance (cd/m$^2$) | Power efficiency (lm/W) | Emission wavelength (nm) |
|---|---|---|---|---|
| Example 23 | 5.8 | 1224 | 2.08 | 517 |
| Example 24 | 5.9 | 1100 | 2.04 | 518 |
| Example 25 | 5.9 | 1120 | 2.05 | 518 |
| Example 26 | 5.2 | 1239 | 2.58 | 517 |
| Example 27 | 5.3 | 1392 | 2.61 | 517 |
| Example 28 | 5.6 | 1198 | 2.69 | 517 |
| Example 29 | 6.1 | 1320 | 2.92 | 518 |
| Example 30 | 5.2 | 1196 | 2.63 | 516 |
| Example 31 | 5.8 | 1208 | 2.47 | 518 |
| Example 32 | 6.1 | 1250 | 2.30 | 518 |
| Comp. Ex. 2 | 6.0 | 1120 | 2.01 | 516 |
| Comp. Ex. 3 | 7.0 | 212 | 0.85 | 518 |
| Comp. Ex. 4 | 6.9 | 253 | 0.90 | 517 |

While the invention has been described in detail and with reference to specific embodiments thereof, it will be apparent to one skilled in the art that various changes and modifications can be made therein without departing from the spirit and scope of the invention.

This application is based on a Japanese patent application filed on Aug. 26, 2005 (Japanese Patent Application No. 2005-246134), a Japanese patent application filed on Apr. 24, 2006 (Japanese Patent Application No. 2006-119912) and a Japanese patent application filed on Aug. 1, 2006 (Japanese Patent Application No. 2006-210262), the entire contents thereof being thereby incorporated by reference.

INDUSTRIAL APPLICABILITY

The 1,3,5-triazine derivative of the invention represented by the formula (1) produces improvement of the electron injection efficiency and also lowering of the driving voltage when used as a composing component of an organic electroluminescence device. In addition, the lowering of driving voltage produces improvement of device lifetime. This is considered to be due to the ability of the nitrogen atom of pyridyl group possessed as a substituent group to undergo interaction with an electrode via its unshared electron pair (e.g., Langmuir, vol. 19, p. 132, 2003). Thus, an organic electroluminescence device having excellent luminescence characteristics and durability can be prepared by the use of the compound of the invention. Industrial value of the invention is remarkable.

The invention claimed is:

1. A 1,3,5-triazine compound which is represented by formula (1):

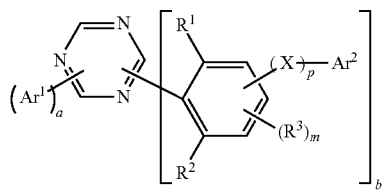

wherein Ar¹ represents a phenyl group, naphthylphenyl group, biphenylyl grow or naphthyl group, which may be substituted with an alkyl group having from 1 to 6 carbon atom(s), $R^1$ and $R^2$ represent a hydrogen atom or a methyl group, $R^3$ represents an alkyl group having from 1 to 4 carbon atom(s), m is an integer of from 0 to 2, wherein $R^3$ may be the same or different from each other when m is 2; X represents a 1,3-phenylene group, 1,4-phenylene group, 1,4-naphthylene group, 1,5-naphthylene group, 2,6-naphthylene group, 2,4-pyridylene group, 2,5-pyridylene group or 2,6-pyridylene group, which may be substituted with an alkyl group having from 1 to 4 carbon atom(s), p is 1 or 2, wherein X may be the same or different from each other when p is 2; $Ar^2$ represents a phenyl group, 1-naphthyl group, 2-naphthyl group, 2-pyridyl group, 3-pyridyl group or 4-pyridyl group, which may be substituted with at least one alkyl group having from 1 to 6 carbon atom(s), with the proviso that at least one pyridine ring is contained in the substituent group $—(X)_p—Ar^2$; a and b are 1 or 2 wherein a+b is 3, Ar¹ may be the same or different from each other when a is 2, and $R^1$, $R^2$, $R^3$, m, X, p and $Ar^2$ may be the same or different from one another when b is 2.

2. The 1,3,5-triazine compound according to claim 1, wherein X is a 1,3-phenylene group, 1,4-phenylene group, 1,4-naphthylene group, 1,5-naphthylene group, 2,6-naphthylene group, 2,4-pyridylene group, 2,5-pyridylene group or 2,6-pyridylene group.

3. The 1,3,5-triazine compound according to claim 1, wherein $R^1$ and $R^2$ are hydrogen atoms.

4. The 1,3,5-triazine compound according to claim 1, wherein m is 0.

5. The 1,3,5-triazine compound according to claim 1, wherein Ar¹ is a phenyl group, p-tolyl group, m-tolyl group, 3,5-dimethylphenyl group, 4-ethylphenyl group, 4-propylphenyl group, 4-isopropylphenyl group, 4-butylphenyl group, 4-tert-butylphenyl group, 4-hexylphenyl group, 4-(1-naphthyl)phenyl group, 4-(2-naphthyl)phenyl group, 3-(1-naphthyl)phenyl group, 3-(2-naphthyl)phenyl group, 4-biphenylyl group, 4'-methylbiphenyl-4-yl group, 4'-tert-butylbiphenyl-4-yl group, 3-biphenylyl group, 3'methylbiphenyl-3-yl group, 3'-tert-butylbiphenyl-3-yl group, 1-naphthyl group, 4-methylnaphthalen-1-yl group, 4-tert-butylnaphthalen-1-yl group, 5-methylnaphthalen-1-yl group, 5-tert-butylnaphthalen-1-yl group, 2-naphthyl group, 6-methylnaphthalen-2-yl group, 6-tert-butylnaphthalen-2-yl group, 7-methylnaphthalen-2-yl group or 7-tert-butylnaphthalen-2-yl group.

6. The 1,3,5-triazine compound according to claim 1, wherein $Ar^2$ is a phenyl group, p-tolyl group, m-tolyl group, 3,5-dimethylphenyl group, 4-ethylphenyl group, 4-propylphenyl group, 4-isopropylphenyl group, 4-butylphenyl group, 4-tert-butylphenyl group, 2-pyridyl group, 3-pyridyl group or 4-pyridyl group.

7. A production method, wherein a 1,3,5-triazine compound represented by formula (1):

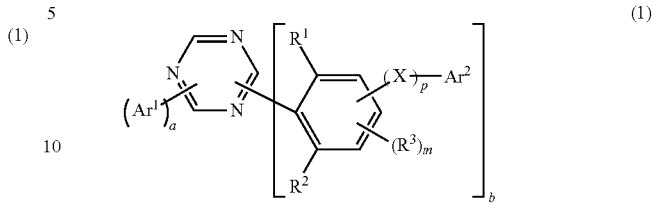

wherein Ar¹ represents a phenyl group, naphthylphenyl group, biphenylyl group or naphthyl group, which may be substituted with an alkyl group having from 1 to 6 carbon atom(s), $R^1$ and $R^2$ represent a hydrogen atom or a methyl group, $R^3$ represents an alkyl group having from 1 to 4 carbon atom(s), m is an integer of from 0 to 2, wherein $R^3$ may be the same or different from each other when m is 2; X represents a 1,3-phenylene group, 1,4-phenylene group, 1,4-naphthylene group, 1,5-naphthylene group, 2,6-naphthylene group, 2,4-pyridylene group, 2,5-pyridylene group or 2,6-pyridylene group, which may be substituted with an alkyl group having from 1 to 4 carbon atom(s), p is 1 or 2, wherein X may be the same or different from each other when p is 2; $Ar^2$ represents a phenyl group, 1-naphthyl group, 2-naphthyl group, 2-pyridyl group, 3-pyridyl group or 4-pyridyl group, which may be substituted with at least one alkyl group having from 1 to 6 carbon atom(s), with the proviso that at least one pyridine ring is contained in the substituent group $—(X)_p—Ar^2$; a and b are 1 or 2 wherein a+b is 3, Ar¹ may be the same or different from each other when a is 2, and $R^1$, $R^2$, $R^3$, m, X, p and $Ar^2$ may be the same or different from one another when b is 2; is obtained by a coupling reaction, in the presence of a metal catalyst, of a substituted aromatic compound represented by formula (2):

wherein X and $Ar^2$ are as defined in the foregoing, q is 0, 1 or 2, M represents a $—ZnR^4$ group, $—MgR^4$ group, $—SnR^5R^6R^7$ group, $—B(OH)_2$ group, $—B=R^8$ group, $—BF_3^-(Z^1)^+$ group or $—SiR^9R^{10}R^{11}$ group, $R^4$ represents a chlorine atom, bromine atom or iodine atom, $R^5$, $R^6$ and $R^7$ represent alkyl groups having from 1 to 4 carbon atom(s), $R^8$ represents a 2,3-dimethylbutane-2,3-dioxy group, ethylenedioxy group, 1,3-propanedioxy group or 1,2-phenylenedioxy group, $(Z^1)^+$ represents an alkali metal ion or a quaternary ammonium ion, and $R^9$, $R^{10}$ and $R^{11}$ represent a methyl group, ethyl group, methoxy group, ethoxy group or chlorine atom; with a 1,3,5-triazine compound represented by formula (3):

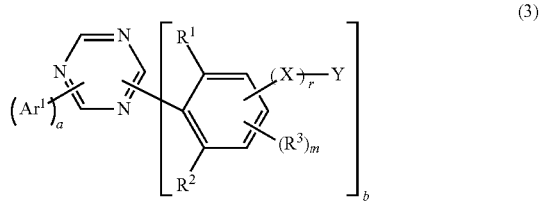

wherein Ar$^1$, a, R$^1$, R$^2$, R$^3$, m, X and b are as defined in the foregoing, r is p-q, and Y represents a leaving group.

8. The production method according to claim 7, wherein X is a 1,3-phenylene group, 1,4-phenylene group, 1,4-naphthylene group, 1,5-naphthylene group, 2,6-naphthylene group, 2,4-pyridylene group, 2,5-pyridylene group or 2,6-pyridylene group.

9. The production method according to claim 7, wherein R$^1$ and R$^2$ are hydrogen atoms.

10. The production method according to claim 7, wherein m is 0.

11. The production method according to claim 7, wherein Ar$^1$ is a phenyl group, p-tolyl group, m-tolyl group, 3,5-dimethylphenyl group, 4-ethylphenyl group, 4-propylphenyl group, 4-isopropylphenyl group, 4-butylphenyl group, 4-tert-butylphenyl group, 4-hexylphenyl group, 4-(1-naphthyl)phenyl group, 4-(2-naphthyl)phenyl group, 3-(1-naphthyl)phenyl group, 3-(2-naphthyl)phenyl group, 4-biphenylyl group, 4'-methylbiphenyl-4-yl group, 4'-tert-butylbiphenyl-4-yl group, 3-biphenylyl group, 3'-methylbiphenyl-3-yl group, 3'-tert-butylbiphenyl-3-yl group, 1-naphthyl group, 4-methylnaphthalen-1-yl group, 4-tert-butylnaphthalen-1-yl group, 5-methylnaphthalen-1-yl group, 5-tert-butylnaphthalen-1-yl group, 2-naphthyl group, 6-methylnaphthalen-2-yl group, 6-tert-butylnaphthalen-2-yl group, 7-methylnaphthalen-2-yl group or 7-tert-butylnaphthalen-2-yl group.

12. The production method according to claim 7, wherein Ar$^2$ is a phenyl group, p-tolyl group, m-tolyl group, 3,5-dimethylphenyl group, 4-ethylphenyl group, 4-propylphenyl group, 4-isopropylphenyl group, 4-butylphenyl group, 4-tert-butylphenyl group, 2-pyridyl group, 3-pyridyl group or 4-pyridyl group.

13. A production method, wherein a 1,3,5-triazine compound represented by formula (1):

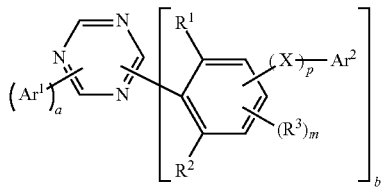

(1)

wherein Ar$^1$ represents a phenyl group, naphthylphenyl group, biphenylyl group or naphthyl group, which may be substituted with an alkyl group having from 1 to 6 carbon atom(s), R$^1$ and R$^2$ represent a hydrogen atom or a methyl group, R$^3$ represents an alkyl group having from 1 to 4 carbon atom(s), m is an integer of from 0 to 2, wherein R$^3$ may be the same or different from each other when m is 2; X represents a 1,3-phenylene group, 1,4-phenylene group, 1,4-naphthylene group, 1,5-naphthylene group, 2,6-naphthylene group, 2,4-pyridylene group, 2,5-pyridylene group or 2,6-pyridylene group, which may be substituted with an alkyl group having from 1 to 4 carbon atom(s), p is 1 or 2, wherein X may be the same or different from each other when p is 2; Ar$^2$ represents a phenyl group, 1-naphthyl group, 2-naphthyl group, 2-pyridyl group, 3-pyridyl group or 4-pyridyl group, which may be substituted with at least one alkyl group having from 1 to 6 carbon atom(s), with the proviso that at least one pyridine ring is contained in the substituent group —(X)$_p$—Ar$^2$; a and b are 1 or 2 wherein a+b is 3, Ar$^1$ may be the same or different from each other when a is 2 and R$^1$, R$^2$, R$^3$, m, X, p and Ar$^2$ may be the same or different from one another when b is 2; is obtained by a coupling reaction, in the presence of a metal catalyst, of a substituted 1,3,5-triazine compound represented by formula (4):

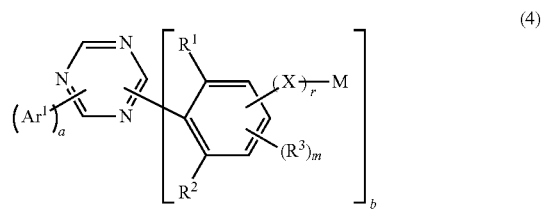

(4)

wherein Ar$^1$, a, R$^1$, R$^2$, R$^3$, m, X and b are as defined in the foregoing, r is p-q, and M represents a —ZnR$^4$ group, —MgR$^4$ group, —SnR$^5$R$^6$R$^7$ group, —B(OH)$_2$ group, —B=R$^8$ group, —BF$_3^-$(Z$^1$)$^+$ group or —SiR$^9$R$^{10}$R$^{11}$ group; with an aromatic compound represented by formula (5):

(5)

wherein X and Ar$^2$ are as defined in the foregoing, Y represents a leaving group, and q is 0, 1 or 2.

14. The production method according to claim 13, wherein X is a 1,3-phenylene group, 1,4-phenylene group, 1,4-naphthylene group, 1,5-naphthylene group, 2,6-naphthylene group, 2,4-pyridylene group, 2,5-pyridylene group or 2,6-pyridylene group.

15. The production method according to claim 13, wherein R$^1$ and R$^2$ are hydrogen atom atoms.

16. The production method according to claim 13, wherein m is 0.

17. The production method according to claim 13, wherein Ar$^1$ is a phenyl group, p-tolyl group, m-tolyl group, 3,5-dimethylphenyl group, 4-ethylphenyl group, 4-propylphenyl group, 4-isopropylphenyl group, 4-butylphenyl group, 4-tert-butylphenyl group, 4-hexylphenyl group, 4-(1-naphthyl)phenyl group, 4-(2-naphthyl)phenyl group, 3-(1-naphthyl)phenyl group, 3-(2-naphthyl)phenyl group, 4-biphenylyl group, 4'-methylbiphenyl-4-yl group, 4'-tert-butylbiphenyl-4-yl group, 3-biphenylyl group, 3'-methylbiphenyl-3-yl group, 3'-tert-butylbiphenyl-3-yl group, 1-naphthyl group, 4-methylnaphthalen-1-yl group, 4-tert-butylnaphthalen-1-yl group, 5-methylnaphthalen-1-yl group, 5-tert-butylnaphthalen-1-yl group, 2-naphthyl group, 6-methylnaphthalen-2-yl group, 6-tert-butylnaphthalen-2-yl group, 7-methylnaphthalen-2-yl group or 7-tert-butylnaphthalen-2-yl group.

18. The production method according to claim 13, wherein Ar$^2$ is a phenyl group, p-tolyl group, m-tolyl group, 3,5-dimethylphenyl group, 4-ethylphenyl group, 4-propylphenyl group, 4-isopropylphenyl group, 4-butylphenyl group, 4-tert-butylphenyl group, 2-pyridyl group, 3-pyridyl group or 4-pyridyl group.

19. The production method according to claim 7, wherein the metal catalyst is a palladium catalyst, a nickel catalyst or an iron catalyst.

20. The production method according to claim 13, wherein the metal catalyst is a palladium catalyst, a nickel catalyst or an iron catalyst.

* * * * *

UNITED STATES PATENT AND TRADEMARK OFFICE
CERTIFICATE OF CORRECTION

PATENT NO.         : 7,994,316 B2
APPLICATION NO.    : 12/064867
DATED              : August 9, 2011
INVENTOR(S)        : T. Yamakawa et al.

It is certified that error appears in the above-identified patent and that said Letters Patent is hereby corrected as shown below:

On Cover Page (56) References Cited, Other Publications, of the printed patent, --Second Chinese Office Action in Chinese Counterpart Application No. 200680031151.7 dated June 3, 2011, accompanied by an English translation-- should be added.

At column 47, line 16 (claim 1, line 4) of the printed patent, "grow" should be --group--.

At column 47, line 55 (claim 5, line 10) of the printed patent, "3'methylbiphenyl-3-yl group" should be --3'-methylbiphenyl-3-yl group--.

At column 50, line 35 (claim 15, line 2) of the printed patent, "atom" should be deleted.

Signed and Sealed this
Third Day of April, 2012

David J. Kappos
*Director of the United States Patent and Trademark Office*